US012569524B2

(12) United States Patent
Besner et al.

(10) Patent No.: US 12,569,524 B2
(45) Date of Patent: Mar. 10, 2026

(54) COMPOSITIONS AND METHODS FOR PREVENTING AND TREATING ANTIBIOTIC INDUCED PATHOLOGIES USING PROBIOTICS IN THE BIOFILM STATE

(71) Applicant: RESEARCH INSTITUTE AT NATIONWIDE CHILDREN'S HOSPITAL, Columbus, OH (US)

(72) Inventors: Gail Besner, Columbus, OH (US); Michael Bailey, Columbus, OH (US); Steven David Goodman, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 912 days.

(21) Appl. No.: 17/287,481

(22) PCT Filed: Oct. 21, 2019

(86) PCT No.: PCT/US2019/057279
§ 371 (c)(1),
(2) Date: Apr. 21, 2021

(87) PCT Pub. No.: WO2020/086487
PCT Pub. Date: Apr. 30, 2020

(65) Prior Publication Data
US 2023/0141737 A1 May 11, 2023

Related U.S. Application Data

(60) Provisional application No. 62/766,527, filed on Oct. 22, 2018.

(51) Int. Cl.
| | |
|---|---|
| *A61K 35/747* | (2015.01) |
| *A61K 9/50* | (2006.01) |
| *A61K 35/74* | (2015.01) |
| *A61K 35/741* | (2015.01) |
| *A61K 35/742* | (2015.01) |
| *A61K 35/744* | (2015.01) |
| *A61K 35/745* | (2015.01) |
| *A61P 31/04* | (2006.01) |

(52) U.S. Cl.
CPC .............. *A61K 35/747* (2013.01); *A61K 9/50* (2013.01); *A61K 35/741* (2013.01); *A61K 35/742* (2013.01); *A61K 35/744* (2013.01); *A61K 35/745* (2013.01); *A61P 31/04* (2018.01)

(58) Field of Classification Search
CPC ...... A61K 35/747; A61K 9/50; A61K 35/741; A61K 35/742; A61K 35/744; A61K 9/5042; A61K 31/7016; A61K 9/5036; A61K 9/5089; A61P 31/04; A23K 10/18; A23L 33/135
See application file for complete search history.

(56) References Cited

U.S. PATENT DOCUMENTS

| | | | |
|---|---|---|---|
| 4,462,982 | A | 7/1984 | Samejima et al. |
| 5,549,908 | A | 8/1996 | Smith et al. |
| 6,486,314 | B1 | 11/2002 | Van Geel-Schutten et al. |
| 6,551,795 | B1 | 4/2003 | Rubenfield et al. |
| 7,241,867 | B2 | 7/2007 | Bakaletz et al. |
| 7,435,595 | B2 | 10/2008 | Boehm et al. |
| 7,638,282 | B2 | 12/2009 | Bakaletz et al. |
| 7,816,086 | B2 | 10/2010 | Bakaletz et al. |
| 7,981,676 | B2 | 7/2011 | Boehm et al. |
| 7,998,490 | B2 | 8/2011 | Bakaletz et al. |
| 8,236,494 | B2 | 8/2012 | Bakaletz et al. |
| 8,283,114 | B2 | 10/2012 | Bakaletz et al. |
| 8,329,187 | B2 | 12/2012 | Lazzari et al. |
| 8,628,917 | B2 | 1/2014 | Bakaletz et al. |
| 8,652,773 | B2 | 2/2014 | Bakaletz et al. |
| 8,758,764 | B2 | 6/2014 | Masignani et al. |
| 8,999,291 | B2 | 4/2015 | Goodman et al. |
| 9,005,682 | B2 | 4/2015 | Sprenger et al. |
| 9,034,642 | B2 | 5/2015 | Bakaletz et al. |
| 9,278,069 | B2 | 3/2016 | Berkland et al. |
| 9,504,739 | B2 | 11/2016 | Berkes et al. |
| 9,554,590 | B2 | 1/2017 | Quintens et al. |
| 9,603,878 | B2 | 3/2017 | Berry et al. |
| 9,610,307 | B2 | 4/2017 | Berry et al. |
| 9,622,956 | B2 | 4/2017 | Schaeffer-Korbylo et al. |
| 9,687,449 | B2 | 6/2017 | Harel |
| 9,713,631 | B2 | 7/2017 | Berkes et al. |

(Continued)

FOREIGN PATENT DOCUMENTS

| | | |
|---|---|---|
| DE | 20 2013 103 204 U1 | 9/2013 |
| EP | 3 113 630 A2 | 1/2017 |

(Continued)

OTHER PUBLICATIONS

Aungst BJ. Absorption enhancers: applications and advances. AAPS J. Mar. 2012;14(1):10-8. doi: 10.1208/s12248-011-9307-4. (Year: 2012).*

Extended European Search Report dated Jun. 23, 2022, from application No. 19877522.3.

Ollech et al., "Use of probiotics in prevention and treatment of patients with Clostridium difficile infection", Best Practice & Research Clinical Gastroenterology, vol. 30, No. 1, Jan. 14, 2016, pp. 111-118.

Shelby et al., "A novel probiotic therapeutic in a murine model of Clostridioides difficile colitis", Gut Microbes, vol. 12, No. 1, Nov. 2020, e1814119, 13 pages.

(Continued)

*Primary Examiner* — Iqbal H Chowdhury

(74) *Attorney, Agent, or Firm* — Foley & Lardner LLP

(57) ABSTRACT

Provided herein are methods for preventing or treating antibiotic induced dysbiosis in a patient by administering to the subject a composition comprising a micro sphere, a bio film-generating probiotic bacterium and a prebiotic, wherein the prebiotic comprises a nutritional supplementation for the probiotic bacterium.

18 Claims, 10 Drawing Sheets

Specification includes a Sequence Listing.

(56) References Cited

U.S. PATENT DOCUMENTS

| | | | |
|---|---|---|---|
| 9,717,765 B2 | 8/2017 | Berkes et al. | |
| 10,369,176 B2 | 8/2019 | Goodman et al. | |
| 10,624,934 B2 | 4/2020 | Goodman et al. | |
| 10,642,934 B2 | 5/2020 | Heck et al. | |
| 10,660,857 B2 | 5/2020 | Prakash et al. | |
| 11,452,748 B2 | 9/2022 | Goodman et al. | |
| 2005/0059633 A1 | 3/2005 | Van Geel-Schuten | |
| 2005/0112235 A1 | 5/2005 | Shefer et al. | |
| 2005/0170504 A1 | 8/2005 | Boehm et al. | |
| 2005/0221439 A1 | 10/2005 | Bakaletz et al. | |
| 2005/0266069 A1* | 12/2005 | Simmons | A23P 10/47 |
| | | | 424/93.45 |
| 2007/0207210 A1 | 9/2007 | Brown et al. | |
| 2007/0264256 A1 | 11/2007 | Bakaletz et al. | |
| 2007/0286822 A1 | 12/2007 | Sanders et al. | |
| 2008/0241226 A1 | 10/2008 | Abeln et al. | |
| 2009/0155912 A1 | 6/2009 | Boehm et al. | |
| 2010/0166771 A1 | 7/2010 | Bakaletz et al. | |
| 2010/0303723 A1 | 12/2010 | Farokhzad et al. | |
| 2010/0310569 A1 | 12/2010 | Bakaletz et al. | |
| 2011/0008493 A1* | 1/2011 | Zorea | A23B 2/92 |
| | | | 426/61 |
| 2011/0027328 A1 | 2/2011 | Baig et al. | |
| 2011/0135646 A1 | 6/2011 | Bakaletz et al. | |
| 2011/0236306 A1 | 9/2011 | Goodman et al. | |
| 2011/0293624 A1 | 12/2011 | Bakaletz et al. | |
| 2012/0128701 A1 | 5/2012 | Goodman et al. | |
| 2012/0189558 A1 | 7/2012 | Prendergast | |
| 2012/0247993 A1 | 10/2012 | Palazzi et al. | |
| 2013/0017204 A1 | 1/2013 | Bakaletz et al. | |
| 2013/0078254 A1 | 3/2013 | Bakaletz et al. | |
| 2014/0005649 A1 | 1/2014 | Burnett et al. | |
| 2014/0010918 A1 | 1/2014 | Quintens et al. | |
| 2014/0120107 A1 | 5/2014 | Bakaletz et al. | |
| 2014/0127221 A1 | 5/2014 | Bakaletz et al. | |
| 2014/0170126 A1 | 6/2014 | Duncker et al. | |
| 2014/0356389 A1 | 12/2014 | Masignani et al. | |
| 2014/0363410 A1 | 12/2014 | Bergonzelli Degonda et al. | |
| 2014/0377192 A1 | 12/2014 | Schaeffer-Korbylo et al. | |
| 2015/0010654 A1 | 1/2015 | Arnold et al. | |
| 2015/0086542 A1 | 3/2015 | Goodman et al. | |
| 2015/0086561 A1 | 3/2015 | Kauvar et al. | |
| 2015/0110838 A1 | 4/2015 | Agrawal | |
| 2015/0166641 A1 | 6/2015 | Goodman et al. | |
| 2015/0173374 A1 | 6/2015 | Majeed et al. | |
| 2015/0197558 A1 | 7/2015 | Kauvar et al. | |
| 2015/0218231 A1 | 8/2015 | Bakaletz et al. | |
| 2015/0247993 A1 | 9/2015 | Ishizaka | |
| 2015/0290140 A1 | 10/2015 | Singh et al. | |
| 2016/0089363 A1 | 3/2016 | Borody | |
| 2016/0095316 A1 | 4/2016 | Goodman et al. | |
| 2016/0120915 A1 | 5/2016 | Blaser et al. | |
| 2016/0143961 A1 | 5/2016 | Berry et al. | |
| 2016/0175440 A1 | 6/2016 | Goodman et al. | |
| 2016/0193258 A1 | 7/2016 | Berry et al. | |
| 2016/0194384 A1 | 7/2016 | Goodman et al. | |
| 2016/0199424 A1 | 7/2016 | Berry et al. | |
| 2016/0223553 A1 | 8/2016 | Sears et al. | |
| 2016/0228476 A1 | 8/2016 | Cutcliffe et al. | |
| 2016/0235792 A1 | 8/2016 | Berry et al. | |
| 2016/0237145 A1 | 8/2016 | Kauvar et al. | |
| 2016/0244489 A1 | 8/2016 | Masignani et al. | |
| 2016/0271188 A1 | 9/2016 | Berry et al. | |
| 2016/0289278 A1 | 10/2016 | Bakaletz et al. | |
| 2017/0056454 A1 | 3/2017 | Berkes et al. | |
| 2017/0056455 A1 | 3/2017 | Berkes et al. | |
| 2017/0128502 A1 | 5/2017 | Berkes et al. | |
| 2017/0182205 A1 | 6/2017 | Zupancic et al. | |
| 2017/0196914 A1 | 7/2017 | Mckenzie et al. | |
| 2017/0196915 A1 | 7/2017 | Czarnecki-Maulden et al. | |
| 2017/0206504 A1 | 7/2017 | Taylor et al. | |
| 2017/0209504 A1 | 7/2017 | Goodman et al. | |
| 2017/0216377 A1 | 8/2017 | Berkes et al. | |
| 2017/0281699 A1 | 10/2017 | Berkes et al. | |
| 2017/0296600 A1 | 10/2017 | Rangavajla | |
| 2017/0312321 A1 | 11/2017 | Rubio Nistal et al. | |
| 2017/0368143 A1 | 12/2017 | Petri et al. | |
| 2018/0000878 A1 | 1/2018 | Goodman et al. | |
| 2018/0071344 A1 | 3/2018 | Berry et al. | |
| 2018/0221422 A1 | 8/2018 | Keshtmand et al. | |
| 2018/0280454 A1 | 10/2018 | Garcia-Rodenas et al. | |
| 2018/0303900 A1 | 10/2018 | Bakaletz et al. | |
| 2020/0155620 A1 | 5/2020 | Goodman et al. | |
| 2021/0100854 A1 | 4/2021 | Goodman et al. | |
| 2021/0290701 A1 | 9/2021 | Besner et al. | |
| 2021/0401904 A1 | 12/2021 | Besner et al. | |
| 2023/0141737 A1 | 5/2023 | Besner et al. | |
| 2023/0285475 A1 | 9/2023 | Goodman et al. | |
| 2024/0075079 A1 | 3/2024 | Goodman et al. | |

FOREIGN PATENT DOCUMENTS

| | | | | |
|---|---|---|---|---|
| JP | 2005-528324 A | 9/2005 | | |
| JP | 2006-512059 A | 4/2006 | | |
| JP | 2010-195786 A | 9/2010 | | |
| JP | 2010-535731 A | 11/2010 | | |
| JP | 2011-102250 A | 5/2011 | | |
| JP | 2011-201840 A | 10/2011 | | |
| JP | 2012-527898 A | 11/2012 | | |
| JP | 2013-510560 A | 3/2013 | | |
| JP | 2013-529893 | 7/2013 | | |
| JP | 2015-503913 A | 2/2015 | | |
| JP | 5670783 B2 | 2/2015 | | |
| JP | 2017-508754 A | 3/2017 | | |
| WO | WO-98/50018 A1 | 11/1998 | | |
| WO | WO-01/11334 A2 | 2/2001 | | |
| WO | WO-02/077183 A2 | 10/2002 | | |
| WO | WO-02/085295 | 10/2002 | | |
| WO | WO-03/083045 A2 | 10/2003 | | |
| WO | WO-2005/111066 A2 | 11/2005 | | |
| WO | WO-2010/138522 A2 | 12/2010 | | |
| WO | WO-2011/000123 A1 | 1/2011 | | |
| WO | WO-2013/007742 A1 | 1/2013 | | |
| WO | WO-2013/088045 A1 | 6/2013 | | |
| WO | WO-2013/098033 A1 | 7/2013 | | |
| WO | WO-2014/067976 A1 | 5/2014 | | |
| WO | WO-2014/121304 A1 | 8/2014 | | |
| WO | WO-2015/134808 A2 | 9/2015 | | |
| WO | WO-2015/177246 A2 | 11/2015 | | |
| WO | WO-2016/066763 A1 | 5/2016 | | |
| WO | WO-2017/205302 A1 | 11/2017 | | |
| WO | WO-2018083336 A1 * | 5/2018 | .......... | A61K 35/747 |
| WO | WO-2018/183355 A1 | 10/2018 | | |
| WO | WO-2018/229216 A1 | 12/2018 | | |
| WO | WO-2020/028871 A1 | 2/2020 | | |

OTHER PUBLICATIONS

Allaker et al., "Non-conventional therapeutics for oral infections," Virulence, vol. 6, No. 3, Apr. 2015, pp. 196-207.

Bakaletz et al., "New strategies to target bacterial biofilms", 28th Annual North American Cystic Fibrosis Conference (NACFC), Atlanta, GA, Oct. 9-11, 2014 (presentation), 2 pages.

Bakaletz et al., "Protection against Development of Otitis Media Induced by Nontypeable Haemophilus influenzae by Both Active and Passive Immunization in a Chinchilla Model of Virus-Bacterium Superinfection," Infecion and Immunity, vol. 67, No. 6, Jun. 1999, pp. 2746-2762.

Bakaletz, "Biofilms can be dispersed by focusing the immune system on a common family of bacterial nucleoid associated proteins", 6th ASM Conference on Biofilms, Miami, FL, Sep. 29-Oct. 4, 2012 (presentation), 5 pages.

Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation), 5 pages.

Bass, J.I.F. et al. (2010) "Extracellular DNA: A Major Proinflammatory Component of Pseudomonas aeruginosa Biofilms," The Journal of Immunology 184:6386-6395.

Beer et al., "Poly (lactic-glycolic) acid copolymer encapsulation of recombinant adenovirus reduces immunogenicity in vivo," Gene Therapy, vol. 5, Jan. 5, 1998, pp. 740-746.

(56) References Cited

OTHER PUBLICATIONS

Ben et al., "Low level of galacto-oligosaccharide in infant formula stimulates growth of intestinal Bifidobacteria and Lactobacilli," World Journal of Gastroenterology, vol. 14, No. 42, Nov. 14, 2008, pp. 6564-6568.

Boyle et al., "Probiotics for the treatment of eczema: a systematic review", Clinical and Experimental Allergy, vol. 39, Apr. 27, 2009, pp. 1117-1127.

Braegger et al., "Supplementation of Infant Formula With Probiotics and/or Prebiotics: A systematic Review and Comment by the ESPGHAN Committee on Nutrition", JPGN, vol. 52, No. 2, Feb. 2011, pp. 239-250.

Burdet et al., "Antibiotic-Induced Dysbiosis Predicts Mortality in an Animal Model of Clostridium difficile Infection", Antimicrobial Agents and Chemotherapy, vol. 62, No. 10, Oct. 2018, Epub Jul. 30, 2018, pp. 1-12.

Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.

Chavarri et al., "Microencapsulation of a probiotic and prebiotic in alginate-chitosan capsules improves survival in simulated gastrointestinal conditions," International Journal of Food Microbiology, vol. 142, Jun. 22, 2010, pp. 185-189.

Chen et al., "Probiotics and the mechanism of necrotizing enterocolitis," Seminars in Pediatric Surgery, vol. 22, 2013, pp. 94-100.

Chen et al., "The effect of immobilization of probiotic Lactobacillus reuteri DPC16 in sub-100 μm microcapsule on food-borne pathogens", World J. Microbial. Biotechnol., vol. 28, No. 6, Mar. 30, 2012, pp. 2447-2452.

Cook et al., "Microencapsulation of a synbiotic into PLGA/alginate multiparticulate gels," International Jounral of Pharmaceutics, vol. 466, Mar. 20, 2014, pp. 400-408.

Cook et al., "Microencapsulation of probiotics for gastrointestinal delivery," Journal of Controlled Release, vol. 162, Jun. 11, 2012, pp. 56-67.

Cornaz Gudet et al., "Simple method of in vitro diffusion of nicotine across procine palatine mucosa", European Journal of Pharmaceutics and Biopharmaceutics, vol. 43, No. 3, Jan. 16, 1997, pp. 259-264.

Crittenden et al., "Synbiotic Microcapsules That Enhance Microbial Viability during Nonrefrigerated Storage and Gastrointestinal Transit", Applied and Environmental Microbiology, vol. 72, No. 3, Mar. 2006, 2280-2282.

Donlan, R.M. et al. (2002) "Biofilms: Survival Mechanisms of Clinically Relevant Microorganisms," Clinical Microbiology Reviews 15(2):167-193.

El Tokhi et al. "Dysregulation of Synaptic Pruning as a Possible Link Between Intestinal 1-10, 58, 59 Microbiota Dysbiosis and Neuropsychiatric Disorders," Journal of Neuroscience Research, 02 Apr. 20, 2020, vol. 98, No. 7 pp. 1335-1369.

Ex Parte Quayle Action on U.S. Appl. No. 15/257,673 dated Sep. 5, 2018, 7 pages.

Extended European Search Report issued in EP 16825137.9 dated Feb. 14, 2019, 9 pages.

Fei Wu, et al., "Development of dextran nanoparticles for stabilizing delicate proteins" Nanoscale Heseorch Letters, 2013, pp. 1-8.

Final Office Action dated Sep. 20, 2021, from U.S. Appl. No. 16/449,320.

Final Office Action on U.S. Appl. No. 15/649,352 dated Apr. 5, 2019, 6 pages.

Final Office Action on U.S. Appl. No. 15/744,725 dated Dec. 17, 2018, 16 pages.

Francavilla et al., "Indications and Recommendations by Societies and Institutions for the Use of Probiotics and Prebiotics in Paediatric Functional Intestinal Disorders", JPGN, vol. 63, Supplemental 1, Jul. 2016, pp. S36-S37.

Goodman et al., "Biofilms can be dispersed by focusing the immune system on a common family of bacterial nucleoid-associated proteins," Mucosal Immunology, vol. 4, No. 6, Nov. 2011, pp. 625-637.

Gur et al. "Stress and the Commensal Microbiota: Importance in Parturition and Infant 1-10, 58, 59 Neurodevelopment," Frontiers in Psychiatry, 02 Feb. 2, 2015. vol. 6, No. 5, pp. 1-6.

Gustave et al., "Targeting bacterial integration host factor to disrupt biofilms associated with cystic fibrosis," Journal of Cystic Fibrosis, vol. 12, No. 4, Nov. 17, 2012, pp. 384-389.

International Search Report and Written Opinion dated Sep. 11, 2020, from application No. PCT/US2020/035976.

Jacob K. Olson, et al., "An Enhanced Lactobacillus Reuteri Biofilm Formulation That Increases Protection Against Experimental Necrotizing Enterocolitis", Am. J: Physiol. Gastrointest. Liver Physiol. 315, May 31, 2018, pp. G408-G419.

Justice et al., "Aberrant Community Architecture and Attenuated Persistence of Uropathogenic Escherichia coli in the Absence of Individual IHF Subunits," PLoS One, vol. 7, No. 10, Oct. 2012, pp. 1-11.

Kadajji et al., "Water Soluble Polymers for Pharmaceutical Applications," Polymers, vol. 3, Nov. 11, 2011, pp. 1972-2009.

Kumari et al., "Biodegradable polymeric nanoparticles based drug delivery systems," Colloids and Surfaces B: Biointerfaces, vol. 75, Sep. 8, 2009, pp. 1-18.

Leonardo et al. "Anxiety as a Developmental Disorder," Neuropsychopharmacology, 12 1-10, 58, 59 Sep. 12, 2007, vol. 33, pp. 134-140.

Lewis et al., "Dietary supplementation with Bifidobacterium lactis NCC2818 from weaning reduces local immunoglobin production in lymphoid-associated tissues but increases systemic antibodies in healthy neonates", British Journal of Nutrition, vol. 110, Mar. 11, 2013, pp. 1243-1252.

Liao et al., "Using probiotics to improve swine gut health and nutrient utilization", Animal Nutrition, vol. 3, Jul. 8, 2017, pp. 331-343.

Mackos et al., "Probiotic Lactobacillus reuteri Attenuates the Stressor-Enhanced Severity of Citrobacter rodentium Infection," Infection and Immunity, vol. 81, Sep. 2013, pp. 3253-3263.

Martin et al., "Probiotics: Role in Pathophysiology and Prevention in Necrotizing Enterocolitis," Seminars in Perinatology, vol. 32, 2008, pp. 127-137.

Mashburn-Warren et al., "Novel method for the depletion of cariogenic bacteria using dextranomer microspheres", Mol. Oral Microbial., May 9, 2017, pp. 475-489.

Navarro et al., "Enhanced Probiotic Potential of Lactobacillus reuteri When Delivered as a Biofilm on Dextranomer Microspheres That Contain Beneficial Cargo," Frontiers in Microbiology, vol. 8, No. 489, Mar. 27, 2017, pp. 1-15.

Non-Final Office Action on U.S. Appl. No. 15/257,673 dated Dec. 22, 2017, 23 pages.

Non-Final Office Action on U.S. Appl. No. 15/649,352 dated Oct. 15, 2018, 21 pages.

Non-Final Office Action on U.S. Appl. No. 15/744,725 dated May 17, 2018, 20 pages.

Non-Final Office Action on U.S. Appl. No. 16/437,921 dated Mar. 12, 2020, 12 pages.

Notice of Allowance on U.S. Appl. No. 15/257,673 dated Dec. 26, 2018, 6 pages.

Notice of Allowance on U.S. Appl. No. 15/257,673 dated Mar. 22, 2019, 8 pages.

Notice of Allowance on U.S. Appl. No. 15/649,352 dated Dec. 23, 2019, 15 pages.

Official Action issued in JP Patent No. 2016-555766 dated Apr. 2, 2019, 10 pages (English Translation).

Olson et al., "An enhanced Lactobacillus reuteri biofilm formulation that increases protection against experimental necrotizing enterocolitis", Am. J. Physiol. Gastrointest. Liver Physiol., vol. 315, Mar. 31, 2018, pp. G408-G419.

Olson et al., "Harvesting the benefits of biofilms: A novel probiotic delivery system for the prevention of necrotizing enterocolitis," Journal of Pediatric Surgery, vol. 51, Feb. 26, 2016, pp. 936-941.

Ornelas-Megiatto et al., "Aerosolized Antimicrobial Agents Based on Degradable Dextran Nanoparticles Loaded with Silver Carbene Complexes", Molecular Pharmaceutics, vol. 9, No. 11, Oct. 1, 2012, pp. 3012-3022.

(56) References Cited

OTHER PUBLICATIONS

Pavia et al., "Antimicrobial activity of nicotine against a spectrum of bacterial and fungal pathogens", J. Med. Microbiol., vol. 49, Dec. 31, 2000, pp. 674-675.

Petreska Ivanovska et al., "Comparative evaluation of viability of encapsulated Lactobacillus casei using two different methods of microencapsulation," International Journal of Pharmaceutical and Phytopharmacological Research, vol. 4, No. 1, pp. 20-24 (Abstract only). Dec. 2014.

Pliszczak et al., "Improvement of an encapsulation process for the preparation of pro- and prebiotics-loaded bioadhesive microparticles by using experimental design," European Journal of Pharmaceutical Sciences, vol. 44, Jun. 25, 2011, pp. 83-92.

Reid et al., "How do probiotics and prebiotics function at distant sites?", Beneficial Microbes, vol. 8, No. 4, Apr. 16, 2017, pp. 521-533.

Restriction Requirement dated Jun. 15, 2021, from U.S. Appl. No. 16/820,463.

Restriction Requirement on U.S. Appl. No. 16/449,320 dated May 18, 2020, 8 pages.

Rezaee et al., "Prebiotics Decrease the Antibacterial Effect of Nano Silver nd Nano TiO2 Particles Against Probiotic Bacteria of Food", Current Nutrition and Food Science, vol. 10, No. 2, Jul. 15, 2013, pp. 88-93.

Rocco et al., "Targeting the HUβ protein prevents porphyromonas gingivalis from entering into preexisting biofilms" Journal of Bacteriology, vol. 200, No. 11, Jun. 2018, pp. 1-11.

Roselli et al., "Immunomodulating effects of probiotics for microbiota modulation, gut heath and disease resistance in pigs," Animal Feed Science and Technology, vol. 233, Jul. 19, 2017, pp. 104-119.

Salas-Jara et al., "Biofilm forming Lactobacillus: New challenges for the development of Probiotics". Microorganisms, vol. 4, No. 35, Sep. 20, 2016, 14 pages.

Salmeron, "Fermented cereal beverages: from probiotic, prebiotic and synbiotic towards Nanoscience designed healthy drinks", Letters in Applied Microbiology, vol. 65, Mar. 31, 2017, pp. 114-124.

Sarmiento-Rubiano et al., "Dietary supplementation with sorbitol results in selective enrichment of lactobacilli in rat intestine," Research in Microbiology, vol. 158, Aug. 2, 2007, pp. 694-701.

Sathyabama et al., "Co-encapsulation of probiotics with prebiotics on alginate matrix and its effect on viability in simulated gastric environment," LWT—Food Science and Technology, vol. 57, Dec. 16, 2013, pp. 419-425.

Sultana et al., "Encapsulation of probiotic bacteria with alginate-starch and evaluation of survival in simulated gastrointestinal conditions and in yoghurt," International Journal of Food Microbiology, vol. 62, May 26, 2000, pp. 47-55.

Thurnheer et al., "Colonisation of gingival epithelia by subgingival biofilms in vitro: role of 'red complex' bacteria," Archives in Oral Biology, vol. 59, No. 9, Sep. 2014, pp. 1-24.

UniProtKB: TrEMBL A0A0E4BIL9. Putative DNA-binding protein HU, 2015, retrieved from www.uniprot.org/uniprot/A0A0E4BIL9.txt?version=3, 1 page.

US Office Action dated Feb. 19, 2021, from U.S. Appl. No. 16/449,320.

Varshosaz, "The promise of chitosan microspheres in drug delivery systems", Expert Opinion on Drug Delivery, vol. 4, No. 3, May 9, 2007, pp. 263-273.

Woischnig et al., "High Affinity Native Human Monoclonal Antibody with Broad Cross-Species Biofilm Disrupting Activity" poster presented at ICAAC Meeting on Sep. 20, 2015, available at www.trellisbio.com/assets/docs/ICAAC%20Biofilm%20Poster%2020150920.pdf., 1 page.

Wu et al., "Preparation of sodium fluoride-loaded gelatin microspheres, characterization and cariostatic studies," J Microencapsul., vol. 21, No. 8, Dec. 2004, pp. 889-903, Abstract Only.

Braga et al., "Efficacy of Bifidobacterium breve and Lactobacillus casei oral supplementation on necrotizing enterocolitis in very-low-birth-weight preterm infants: a double-blind, randomized, controlled trial", Am J Clin Nutr, Jan. 2011, vol. 93, pp. 81-86. doi: 10.3945/ajcn.2010.29799.

Desiderio, et al. "Intraphagocytic Killing of Salmonella typhimurium by Liposome-Encapsulated Cephalothin", The Journal of Infectious Diseases, vol. 148, No. 3, Sep. 1983, pp. 563-570.

Herrington et al., "Anxiety and social deficits have distinct relationships with amygdala function in autism spectrum disorder", Social Cognitiue and Affective Neuroscience, Jun. 2016, pp. 907-914. doi: 10.1093/scan/nsw015.

Jones, S.E., et al., "Probiotic Lactobacillus reuteri biofilms produce antimicrobial and anti-inflammatory factors," BMC Microbiology, Feb. 2009, vol. 9, 35, 9 pages.

Lin et al., "Effect of size on the in vitro/in vivo drug release and degradation of exenatide-loaded PLGA microspheres", journal of Drug Delivery Science and Technology, 2018, vol. 45, pp. 346-356.

Navarro, et al. "Enhanced Probiotic Potential of Lactobacillus reuteri When Delivered as a Biofilm on Dextranomer Microspheres That Contain Beneficial Cargo", Frontiers in Microbiology, vol. 8, Mar. 8, 2017, 15 pages. XP055928403, DOI: 10.3389/fmicb.2017.00489.

US Final Office Action dated Jun. 15, 2022, from U.S. Appl. No. 16/820,463, 7 pages.

US Final Office Action on U.S. Appl. No. 16/961,910, dated Jan. 24, 2024, 15 pages.

US Non-Final Office Action dated Dec. 27, 2021, from U.S. Appl. No. 16/820,463, 19 pages.

US Non-Final Office Action dated Feb. 3, 2022, from U.S. Appl. No. 16/437,921, 11 pages.

US Non-Final Office Action dated Jul. 19, 2023, for U.S. Appl. No. 16/961,910, 12 pages.

US Non-Final Office Action dated Oct. 11, 2023, for U.S. Appl. No. 17/885,446.

US Notice of Allowance dated Jun. 1, 2022, from U.S. Appl. No. 16/437,921, 10 pages.

US Notice of Allowance dated Jun. 30, 2022, from U.S. Appl. No. 16/820,463, 10 pages.

Sheretz et al., "The prevalence of Clostridium difficile and toxin in a nursery population: A Comparison between patients with necrotizing enterocolitis and an asymptomatic group", The Journal of Pediatrics, Mar. 1982. vol. 100, Issue 3, pp. 435-439.

Tabouy et al., "Dysbiosis of microbiome and probiotic treatment in a genetic model of autism spectrum disorders," Brain, Behavior, and Immunity, 73, 2018, pp. 310-319.

U.S. Advisory Action dated Jul. 2, 2024, for U.S. Appl. No. 16/961,910.

U.S. Final Office Action dated Jul. 1, 2024, for U.S. Appl. No. 17/885,446.

U.S. Non-Final Office Action dated May 9, 2024, for U.S. Appl. No. 17/265,505.

U.S. Non-Final Office Action dated Sep. 27, 2024, for U.S. Appl. No. 16/961,910.

U.S. Final Office Action dated Jan. 28, 2025, for U.S. Appl. No. 16/961,910.

U.S. Final Office Action dated Nov. 13, 2024, for U.S. Appl. No. 17/265,505.

Hickey et al., "Neurodevelopmental outcomes following necrotizing enterocolitis," Seminars in Fetal and Neonatal Medicine, Aug. 17, 2018, 23, pp. 426-432.

Akar et al., "Impact of oral probiotics on neurodevelopmental outcomes in preterm infants," The Journal of Maternal-Fetal & Neonatal Medicine, 2017, vol. 30, Issue 4, Abstract, 2 pages.

Schreiber et al., "Lactobacillus reuteri prevents colitis by reducing P-selectin-associated leukocyte- and platelet-endothelial cell interactions," American Journal of Physiology—Gastrointestinal and Liver Physiology, vol. 296, No. 3, 2009, pp. G534-G542.

Schwab et al., "Sucrose utilization and impact of sucrose on glycosyltransferase expression in Lactobacillus reuteri," Systematic and Applied Microbiology, 2007, 30, pp. 433-443.

U.S. Notice of Allowance dated Jun. 18, 2025, for U.S. Appl. No. 16/961,910.

US Non-Final Office Action dated Apr. 15, 2025, for U.S. Appl. No. 17/955,413.

(56)  References Cited

OTHER PUBLICATIONS

US Non-Final Office Action dated Mar. 26, 2025, for U.S. Appl. No. 17/265,505.

* cited by examiner

Figures 9, 10:
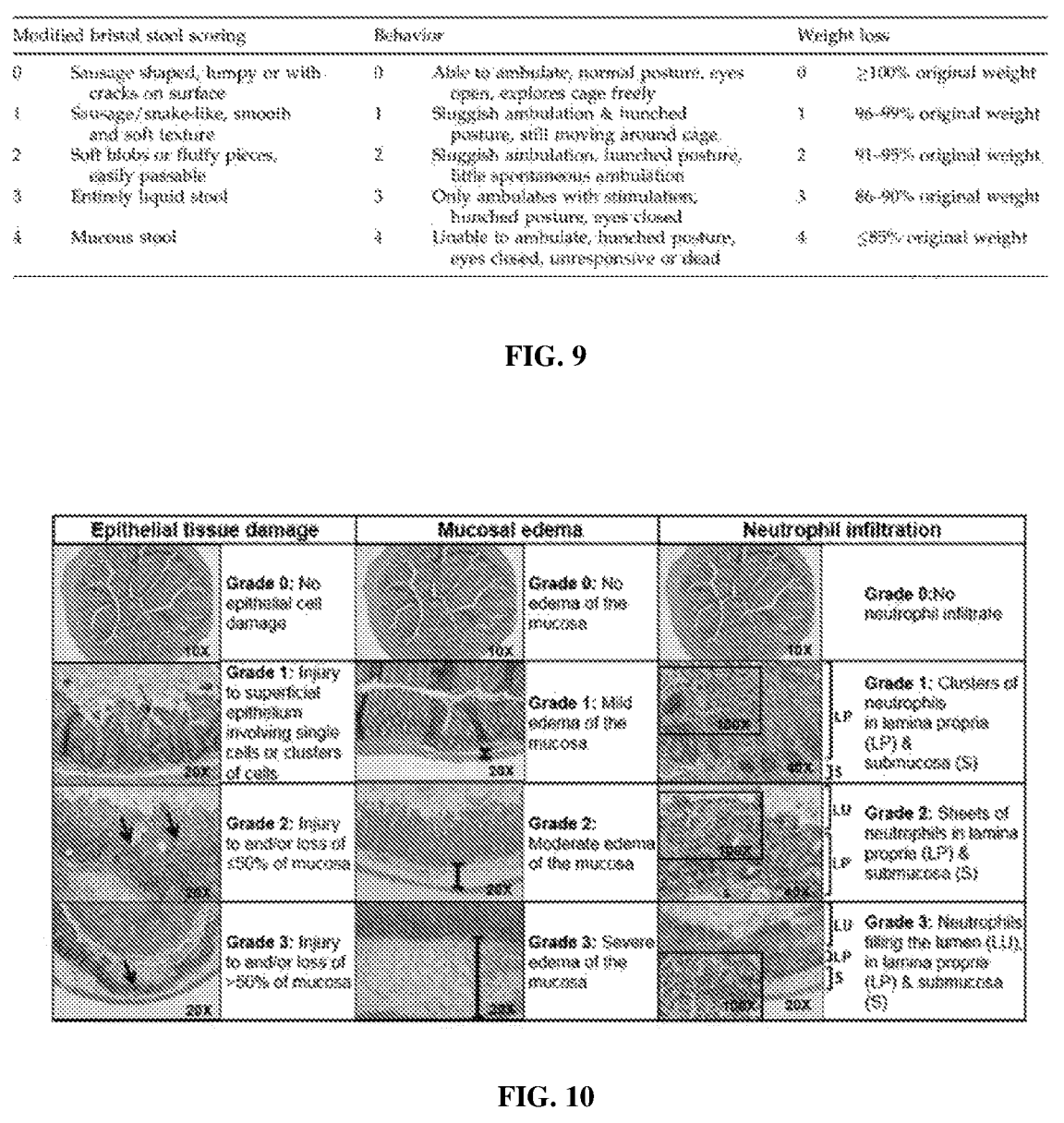

| Modified bristol stool scoring | | Behaviour | | Weight loss | |
|---|---|---|---|---|---|
| 0 | Sausage shaped, lumpy or with cracks on surface | 0 | Able to ambulate, normal posture, eyes open, explores cage freely | 0 | ≥100% original weight |
| 1 | Sausage/snake-like, smooth and soft texture | 1 | Sluggish ambulation & hunched posture, still moving around cage | 1 | 96-99% original weight |
| 2 | Soft blobs or fluffy pieces, easily passable | 2 | Sluggish ambulation, hunched posture, little spontaneous ambulation | 2 | 91-95% original weight |
| 3 | Entirely liquid stool | 3 | Only ambulates with stimulation, hunched posture, eyes closed | 3 | 86-90% original weight |
| 4 | Mucous stool | 4 | Unable to ambulate, hunched posture, eyes closed, unresponsive or dead | 4 | ≤85% original weight |

Untreated        Antibiotics+PBS        Antibiotics+L-DM
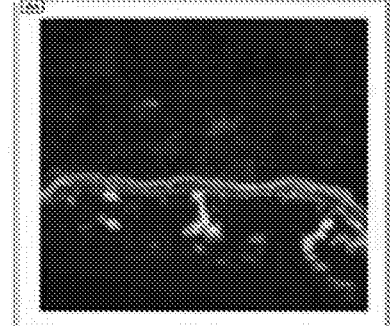 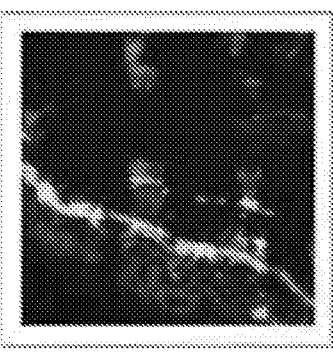 
FIG. 15

COMPOSITIONS AND METHODS FOR PREVENTING AND TREATING ANTIBIOTIC INDUCED PATHOLOGIES USING PROBIOTICS IN THE BIOFILM STATE

CROSS-REFERENCE TO RELATED APPLICATION

This application is a national stage application under 35. U.S.C. § 371 of PCT Application No. PCT/US2019/057279, filed Oct. 21, 2019, which in turn claims priority under 35 U.S.C. § 119(e) to U.S. Provisional Application No. 62/766, 527, filed Oct. 22, 2018, the contents of each of which are hereby incorporated by reference into the present disclosure.

SEQUENCE LISTING

The instant application contains a Sequence Listing which has been submitted electronically in ASCII format and is hereby incorporated by reference in its entirety. Said ASCII copy, created on Apr. 21, 2021, is named 106887-7812_SL.TXT and is 851 bytes in size.

TECHNICAL FIELD

This disclosure relates to compositions and methods for preventing or treating antibiotic induced dysbiosis and restoring the protective mucosal layer of the intestines.

BACKGROUND

There is no doubt that antibiotics save lives and communities. Antibiotic use has been likened to a four-edged sword against bacteria. Blaser et al. (2016) Science 352(6285):544-545. The first two edges are that the drugs treat patients (edge 1) and communities (edge 2) by impeding the spread of infection and disease. The third edge is the rise of antibiotic resistant bacteria and incident costs to society. The fourth edge, more recently discovered, is the cost to the individual's microbiome—previously unappreciated collateral damage.

*Clostridium difficile* infection (CDI) is an example of the "collateral damage" of antibiotic use. CDI is a significant public health burden with over 450,000 new cases leading to over 29,000 deaths and $4.8 billion dollars of excess medical costs annually. After receiving antibiotics, the gut microbiota of the colon is altered and *C. difficile* spores flourish and transform into active bacterial cells. These cells then secrete Toxin A and Toxin B which cause symptomatic disease. The toxins then penetrate the intestinal epithelium and cause injury. The toxins cause neutrophil and macrophage infiltration into the injured colon, leading to further damage.

Current treatment includes the administration of antibiotics for acute disease or fecal transplant for relapsed disease. However, many patients are still not cured, and those requiring surgery have up to 55% mortality. Thus, a need exists for an effective therapy. This disclosure satisfies this need and provides related advantages as well.

SUMMARY

There are no FDA recognized treatments for prevention or treatment of antibiotic induced dysbiosis particularly for opportunistic infections caused by *C difficile*. This disclosure provides probiotic formulations that prevent and treat dysbiosis caused by antibiotic treatments. It has been shown that in some aspects, antibiotic treatment destroys the protective mucosal barrier of the intestines (see FIG. 3A). Applicants show herein that administration of the claimed compositions and methods restores the intestinal mucosal barrier. Thus, in one aspect, the methods and compositions bolter gut ("intestinal") integrity which in turn can protect the gut from pathologies including CDI. This result was surprising and unexpected. In one aspect, the composition is administered preceding or following any antibiotic treatment regimen, especially when used in conjunction with recurring infectious disease such as *C. difficile* infection. This approach can also be used prior to any antibiotic course but particularly in hosts that are immune compromised (e.g. prior to or after chemotherapy treatments).

In one aspect, a method is provided for reversing antibiotic induced dysbiosis in a patient in need thereof, comprising, or alternatively consisting essentially of, or yet further consisting of, administering to the subject a composition comprising a microsphere, a biofilm-generating probiotic bacterium and a prebiotic, wherein the prebiotic comprises a nutritional supplementation for the probiotic bacterium, that is optionally administered prior to, concurrently or subsequent to administration of the antibiotic. Any FDA approved antibiotic is intended within the scope of this disclosure, e.g., kanamycin, gentamycin, colistin, metronidazole, vancomycin, ceftazidime, avibactam, obiltoxaximab, bezlotoxumab, delafloxacin, vaborbactam, babomer, ozenoxacin, malacidine, teixobactin, and combinations thereof. A list of FDA approved antibiotics is available at drugs.com/article/antibiotics.html (last accessed on Sep. 25, 2018). In another aspect, the methods are practice by administering one or more microspheres that comprise Sephadex or Sephadex G-25, and comprises maltose and *L. reuteri* (e.g., ATCC 23272), the microsphere optionally also having a biofilm coating on all or part of the external surface of the microsphere. In another aspect, the methods are practice by administering one or more microspheres that comprise Sephadex or Sephadex G-25, and comprise maltose and *L. reuteri* (e.g., ATCC 23272), the microsphere also having a biofilm coating all or part of the external surface of the microsphere. The one or more microspheres may be the same or different from each other, e.g., one or more of diameter, composition and CFU/ml of *L. reuteri*.

In another aspect, a method is provided for preventing or treating *C difficile* infection caused by antibiotic induced dysbiosis in a patient in need thereof, comprising, or alternatively consisting essentially of, or yet consisting of, administering to the subject a composition comprising a microsphere, a biofilm-generating probiotic bacterium and a prebiotic, wherein the prebiotic comprises a nutritional supplementation for the probiotic bacterium, that is optionally administered prior to, concurrently or subsequent to administration of the antibiotic. In a further aspect, the treatment comprises restoration of the protective mucosal layer of the intestine. In another embodiment, the treatment comprises one or more of maintaining the epithelial barrier, supporting epithelial cell integrity (e.g., reduce apoptosis, maintain tight junction proteins) or supporting goblet cell production of mucous. In another aspect, the methods are practice by administering one or more microspheres that comprise Sephadex or Sephadex G-25, and comprise maltose and *L. reuteri* (e.g., ATCC 23272), the microsphere optionally also having a biofilm coating all or part of the external surface of the microsphere. The one or more microspheres may be the same or different from each other, e.g., one or more of diameter, composition and CFU/ml of *L. reuteri*.

The methods can be administered in amounts effective to treat or prevent the disease or condition and will vary with the subject, disease or symptom. For these methods, the subject is a mammal, e.g., an animal, a mammal or a human patient that is optionally an infant or juvenile. In one aspect, the subject is immunocompromised.

While the disclosed methods are useful for treating antibiotic induced dysbiois that results in CDI, other antibiotic induced illnesses are treated, e.g., metabolic perturbations that affect adiposity and bone growth, and alterations in immunologic development. See Blasar et al. (2016), supra. Any FDA approved antibiotic is intended within the scope of this disclosure, e.g., kanamycin, gentamycin, colistin, metronidazole, vancomycin, ceftazidime, avibactam, obiltoxaximab, bezlotoxumab, delafloxacin, vaborbactam, babomer, ozenoxacin, malacidine, teixobactin, and combinations thereof. A list of FDA approved antibiotics is available at drugs.com/article/antibiotics.html (last accessed on Sep. 25, 2018).

The methods of this disclosure also comprise, or alternatively consist essentially of, or yet further consist of, administering a composition comprising, or alternatively consisting essentially of, or yet further consisting of, a biocompatible microsphere, a biofilm-generating probiotic bacterium and a prebiotic, wherein the prebiotic comprises, or alternatively consisting essentially of, or yet consisting of, a nutritional supplementation for the probiotic bacterium. In one embodiment, the prebiofilmic comprises an agent that supports biofilm formation and durability and/or an agent that improves the probiotic bacterium's ability to increase mucous production. In another aspect, the methods are practice by administering one or more microspheres that comprises Sephadex or Sephadex G-25, and comprises maltose and *L. reuteri* (e.g., ATCC 23272), the microsphere optionally also having a biofilm coating all or part of the external surface of the microsphere. The one or more microspheres may be the same or different from each other, e.g., one or more of diameter, composition and CFU/ml of *L. reuteri*.

In one aspect of the methods as disclosed herein, the microsphere further comprises a partial or complete biofilm coating on the external surface of the microsphere.

In another aspect, provided herein are methods of reversing antibiotic induced dysbiosis in a patient in need thereof, comprising or consisting essentially of, or yet further consisting of administering an effective about of a microsphere composition, the composition comprising, or consisting essentially of, or yet further consisting of a plurality of microspheres each comprising cross-linked dextran; and a water-soluble carbohydrate selected from the group consisting of maltose, sucrose, and combinations thereof; *L. reuteri*; and a pharmaceutically acceptable carrier. In one aspect, the cross linked dextran is dextran cross-linked with epicholorhydine and the separately or in combination, the plurality of microspheres each have a diameter of about 1 to about 75 microns. In another aspect, the *L. reuteri* is strain ATCC 23272. In a yet further aspect, the *L. reuteri* is adhered to the microspheres, e.g., the external surface of the microspheres. In another aspect, the composition comprises between about $1\times10^7$ and $1\times10^{10}$ CFU/ml of *L. reuteri*. In a further aspect, the composition comprises about 5 mg/ml of the microspheres. In another aspect, the methods are practice by administering one or more microspheres that comprise Sephadex or Sephadex G-25, and comprise maltose and *L. reuteri* (e.g., ATCC 23272), the microsphere optionally also having a biofilm coating all or part of the external surface of the microsphere. The one or more microspheres may be the same or different from each other, e.g., one or more of diameter, composition and CFU/ml of *L. reuteri*.

Also provided are methods for treating preventing or treating *C difficile* infection in a patient having antibiotic induced dysbiosis, the methods comprising, or alternatively consisting essentially of, or yet further consisting of, administering a composition comprising, consisting essentially of, or yet further consisting of about $1\times10^7$ and $1\times10^{10}$ CFU/ml of *L. reuteri*; and a plurality of microspheres, wherein each microsphere comprises cross-linked dextran, and a water-soluble carbohydrate selected from the group consisting of maltose, sucrose, and combinations thereof. In one aspect, the *L. reuteri* is strain ATCC 23272. In another aspect, the methods are practice by administering one or more microspheres that comprise Sephadex or Sephadex G-25, and comprise maltose and *L. reuteri* (e.g., ATCC 23272), the microsphere optionally also having a biofilm coating all or part of the external surface of the microsphere. The one or more microspheres may be the same or different from each other, e.g., one or more of diameter, composition and CFU/ml of *L. reuteri*.

In one aspect, the composition further comprises, or alternatively consists essentially of, or yet further consisting of, a carrier, such as a pharmaceutically acceptable carrier or a biocompatible scaffold. The compositions can be administered in a single or multiple doses. One of skill in the art can determine when the method has been successful, e.g., by assaying subject samples for antimicrobial and/or anti-inflammatory markers.

The compositions are formulated for in vivo or ex vivo use. For use in vivo, the compositions are formulated for administration orally, vaginally, nasally (inhalation), intravenously or intramuscularly (injectable), topically, as a suppository, as a spray (aerosol administration), dry application by admixing in the soil, as a solute (for admixing with an aqueous environment). In one aspect, they are formulated in a dosage form. Suitable dosage forms include, but are not limited to a suppository, a powder, a liquid, a capsule, a chewable tablet, a swallowable tablet, a buccal tablet, a troche, a lozenge, a soft chew, a solution, a suspension, a spray, a tincture, a decoction, an infusion, and combinations thereof.

This disclosure also provides a method for preparing the above-noted composition, the method comprising, or alternatively consisting essentially of, or yet further consisting of, admixing a biocompatible microsphere with a biofilm-generating probiotic bacterium, a prebiotic, and in one aspect, further admixing a prebiofilmic. In a further aspect, the method further comprises, or alternatively consists essentially of, or yet further consists of, admixing an effective amount of one or more of: a nutritional supplement for the probiotic bacterium, a drug active against a pathogen or invertebrate, or a chemical reductant and/or molecule that promote adsorption (in the core or on the surface of the microsphere) and/or molecules that promote absorption (in the core or on the surface of the microsphere).

In some embodiments, a kit is provided comprising, or alternatively consisting essentially of, or yet consisting of, a composition as described herein and instructions for use in the methods as described herein.

Typically, the strategy is to administer multiple or daily doses of probiotic to show any effect, and once administration is terminated the beneficial effect does not continue. The biofilm-based probiotic formulation (Lr+DM-maltose) works as a single administration and has been previously shown to work in another gastrointestinal disease model (Olson 2018 Am J Physiol Gastrointest Liver Physiol DOI: 10.1152/ajpgi.00078.2018). The Lr probiotic biofilm forms on the surface of polysaccharide microspheres via an extracellular protein (GtfW) and is enhanced by addition of the protein's substrate, maltose (Navarro 2017 Front Microbiol 8: 489 DOI: 10.3389/fmicb.2017.00489) (CA2941694A1). The probiotic biofilms persist better within the host compared to planktonic probiotic (Olson (2018) Am J Physiol Gastrointest Liver Physiol DOI: 10.1152/ajpgi.00078.2018), thus negating the need for repeated dosing and establishing a more effective treatment and preventative strategy for pathogen-associated diseases. As it pertains to the data shown above, the probiotic biofilms adhered to microspheres (Lr+DM-maltose) is a novel treatment strategy for gastrointestinal recovery after intensive antibiotic treatment, as well as a preventative to stop a disease-causing pathogen from establishing infection.

Figure 1A:
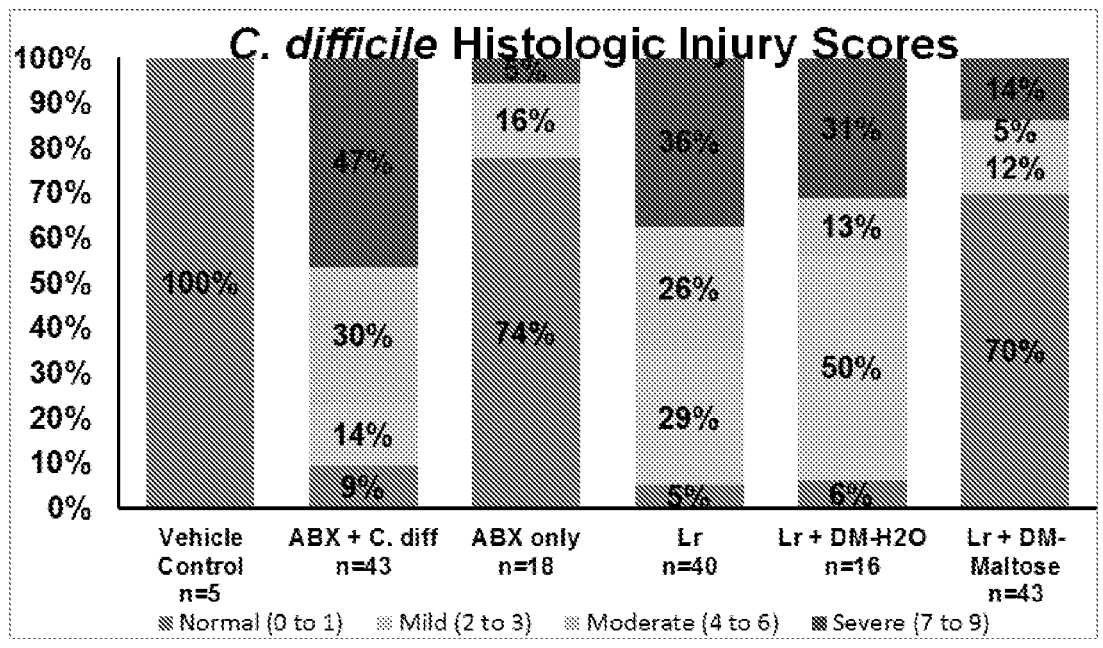
FIG. 1A shows the results of an experiment wherein C57BL/6 mice were given an antibiotic cocktail in water containing kanamycin (0.4 mg/ml), gentamicin (0.035 mg/ml), colistin (850 U/ml), metronidazole (0.215 mg/ml), and vancomycin (0.045 mg/ml) for four days (eight days prior to *Clostridium difficile* administration), followed by intraperitoneal injection of clindamycin (10 mg/kg) (two days prior to *Clostridium difficile* administration). Probiotic was administered via oral gavage 24 hours prior to *Clostridium difficile* administration in the form of planktonic *L. reuteri* (Lr), Lrbiofilms on microspheres filled with water (Lr+DM-H2O), or Lr biofilms on microspheres filled with maltose (Lr+DM-maltose). Probiotic dosage was $2 \times 10^8$ CFU of *L. reuteri*, 2 mg of DM, and 8 µl of 1M maltose (final 3.4%). *C. difficile* was administered via oral gavage at a dose of $1 \times 10^7$ CFU. Mice were observed for symptoms of sickness including behavioral changes, stool characteristics adapted from the Bristol stool scoring system, and weight loss. Mice were euthanized based on accumulation of symptoms, or died from disease. All surviving mice were sacrificed six days after *C. difficile* administration. The cecum and colon were collected for histopathologic analysis. Histology scoring was done blindly based on epithelial tissue damage, mucosal edema, and neutrophil infiltration. Mice administered vehicle control (FIG. 1A column 1—no antibiotic treatment, sterile PBS solution in place of Lr and *C. difficile* administration) had no external or histological signs of disease. Mice administered antibiotics only (FIG. 1A column 3—cocktail of antibiotics and IP clindamycin, sterile PBS solution in place of Lr and *C. difficile* administration) showed some signs of histologic injury. This is consistent with published studies showing antibiotic use causes a disruption of the gastrointestinal microbiome, which can lead to severe diarrhea and colitis. The majority (74%) of mice show little to no sign of histologic injury. Mice administered antibiotics followed by *C. difficile* (FIG. 1A column 2—cocktail of antibiotics and IP clindamycin, sterile PBS solution in place of Lr, and *C. difficile* administered at $1 \times 10^7$ CFU) showed extreme signs of intestinal injury. The majority (77%) of mice were scored as moderate to severe histologic injury, with the majority from this group dying from injury. Mice administered antibiotics followed by planktonic Lr, and *C. difficile* (FIG. 1A column 4—antibiotic cocktail+IP clindamycin, $2 \times 10^8$ CFU Lr, $1 \times 10^7$ CFU *C. difficile*) showed extreme signs of intestinal injury similar to when no probiotic treatment at all (column 2). The majority (62%) of mice were scored as moderate to severe histologic injury, with the majority from this group dying from injury. Mice administered antibiotics followed by a weak biofilm of Lr+DM-H2O and *C. difficile* (FIG. 1A column 5—antibiotic cocktail+IP clindamycin, $2 \times 10^8$ CFU Lr+2 mg DM-H2O, $1 \times 10^7$ CFU *C. difficile*) showed slightly improved intestinal injury compared to planktonic Lr (column 4) and no probiotic (column 2), but with 44% of mice still having moderate to severe histologic scores and very few (6%) having normal gastrointestinal scores. Mice administered antibiotics followed by biofilm Lr+DM-maltose and *C. difficile* (FIG. 1A column 6—antibiotic cocktail+IP clindamycin, $2 \times 10^8$ CFU *L. reuteri*+2 mg DM-maltose, $1 \times 10^7$ CFU *C. difficile*) showed dramatically improved intestinal injury compared to planktonic probiotic (column 4) and weak biofilm probiotic (column 5). Mice showing no intestinal injury (70%) was similar to the antibiotic-only group (74%, column 3, no *C. difficile* administration). The failure of planktonic Lr to prevent *C. difficile* colitis is consistent with previous work with *C. difficile* and other bacterial disease models that probiotic administration in and of itself is not enough to prevent or treat disease states. With *C. difficile* infection specifically, there is some evidence that probiotic administration alone can in fact exacerbate the disease (Spinler 2016 Anaerobe 40: 54-57 DOI: 10.1016/j.anaerobe.2016.05.008).
Figure 1B:
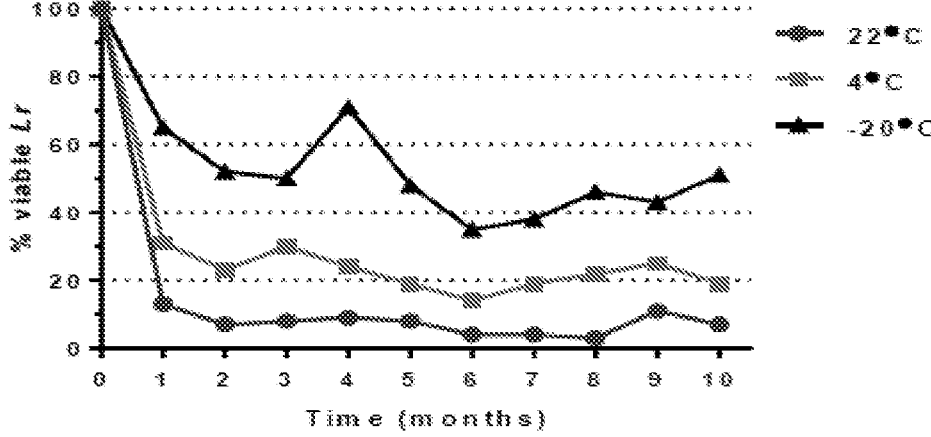

FIG. 1B shows the stability of reconstituted microspheres as a percent viability of the bacteria (Lr) compared to the starting concentration.

Figure 2:
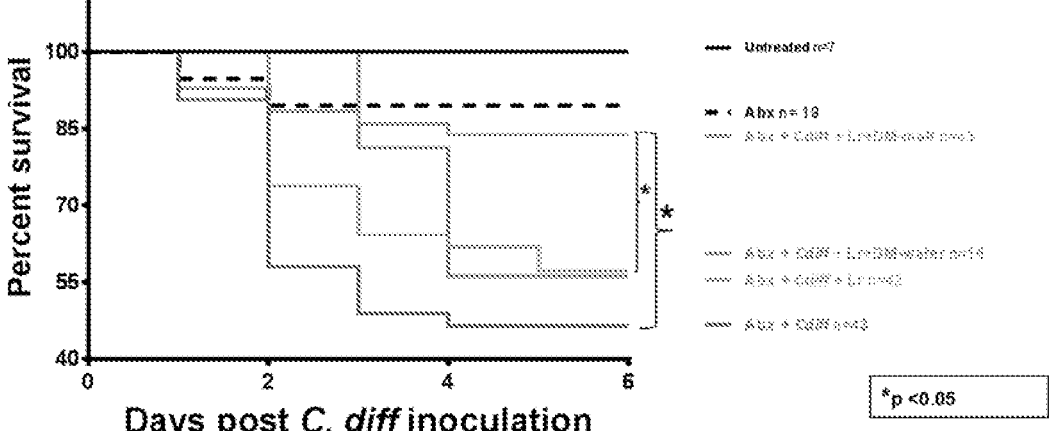

FIG. 2 is a graph showing mice survival of the mouse populations of FIG. 1A.

Figure 3:
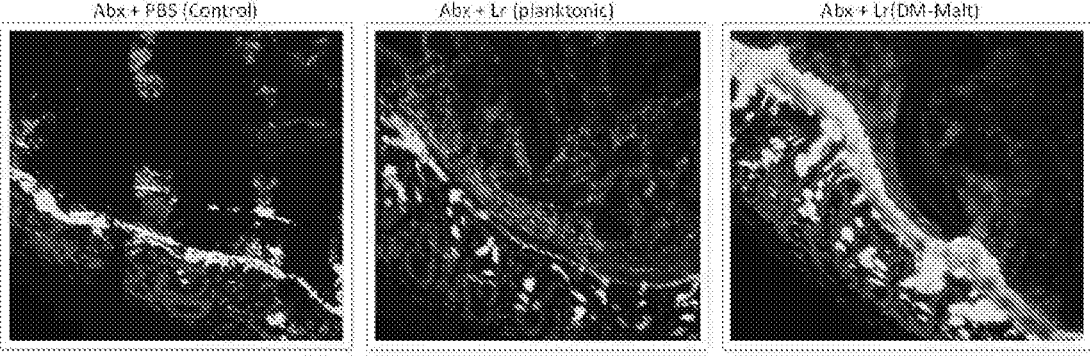

FIG. 3: C57BL/6 mice were given an antibiotic cocktail in water containing kanamycin (0.4 mg/ml) gentamicin (0.035 mg/ml), colistin (850 U/ml), metronidazole (0.215 mg/ml), and vancomycin (0.045 mg/ml) for four days followed by intraperitoneal injection of clindamycin (10 mg/kg). Timing is similar to experiments as disclosed herein, but no *C. difficile* is administered. Probiotic was administered via oral gavage 24 hours after the intraperitoneal injection of clindamycin. Colon integrity was assessed 96 hr after probiotic administration using fluorescence microscopy to assess epithelial integrity and mucous thickness by staining epithelial cell nucleus (DAPI stain) and with fluorescent antibodies to Muc2 (found in intestinal mucous). Fluorescence in situ hybridization (FISH) was used to visualize the bacteria by using FISH probes to the V4 region of the 16S rRNA gene. Animals treated with the antibiotic cocktail had widespread epithelial disruption and breakdown of the mucous layer. Bacteria were seen adhering to intestinal epithelial cells. Treatment with planktonic Lr increased the distance between the epithelial cells and gut bacteria, but the mucous layer was still disrupted. However, the mucous layer was thickest in animals given Lr with dextranomer microspheres loaded with maltose (Lr+DM-Malt).

Figure 4:
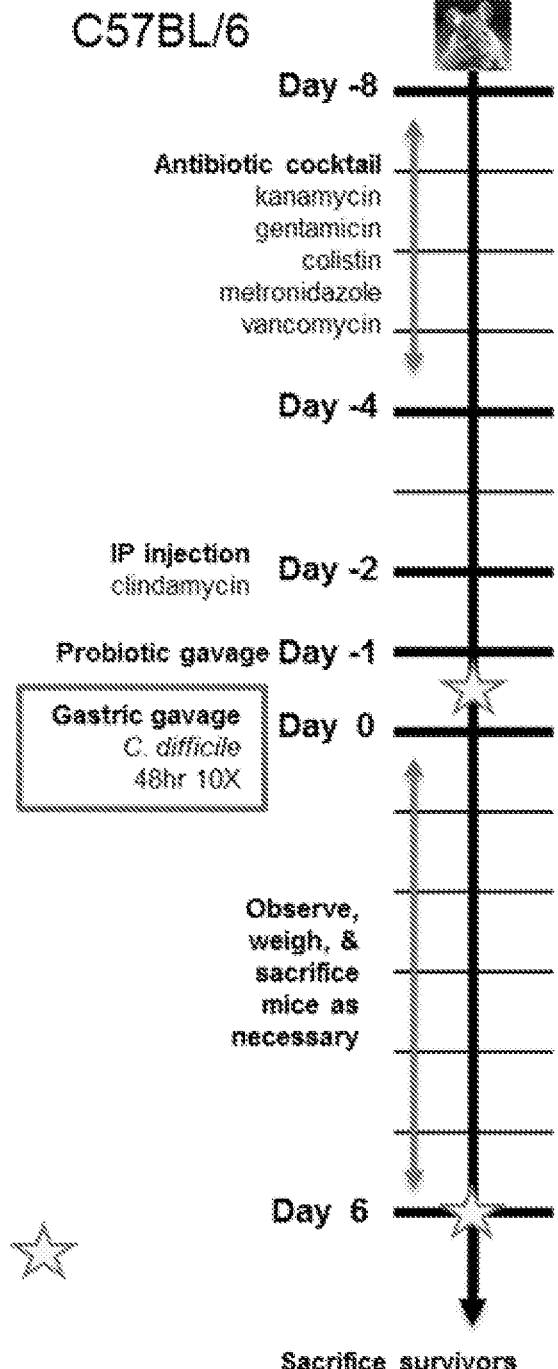

FIG. 4: Experimental design of *C. difficile* infection animal model.

Figure 5:
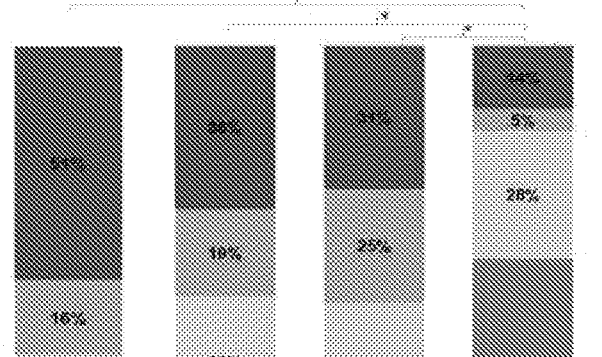

FIG. 5 is a *C. difficile* clinical injury scoring of animals subjected to experimental CDI. Mice were exposed to experimental CDI, and received the treatments indicated underneath each bar. Daily clinical sickness scores were determined, and the highest score was used for analysis. *$p < 0.05$.

Figures 6A, 6B, 6C, 6D:
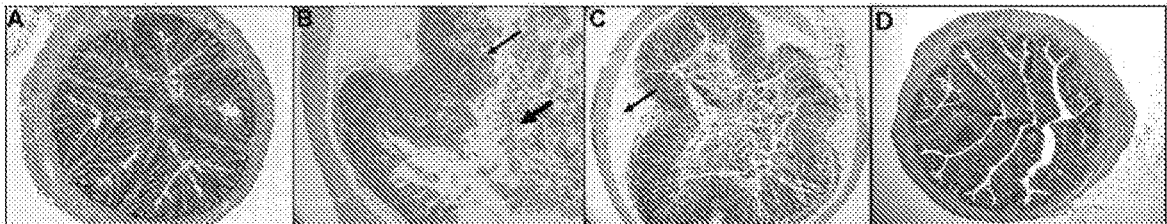

FIGS. 6A-6D show typical histologic appearance of colonic tissue obtained from a mouse exposed to: (FIG. 6A) no injury (control), (FIGS. 6B and C) experimental CDI as in FIG. 1 but with no treatment (vehicle control only), and (FIG. 6D) experimental CDI with Lr+DM-maltose treatment. FIG. 6B demonstrates ulcerative colitis with epithelial damage and necrosis (thin arrow), and release of inflammatory cells and necrotic cells into the intestinal lumen (thick arrow). FIG. 6C demonstrates extensive submucosal edema (arrow). FIG. 6D demonstrates nearly normal histology in the colon of a mouse exposed to CDI but treated with Lr+DM-maltose.

Figure 7:
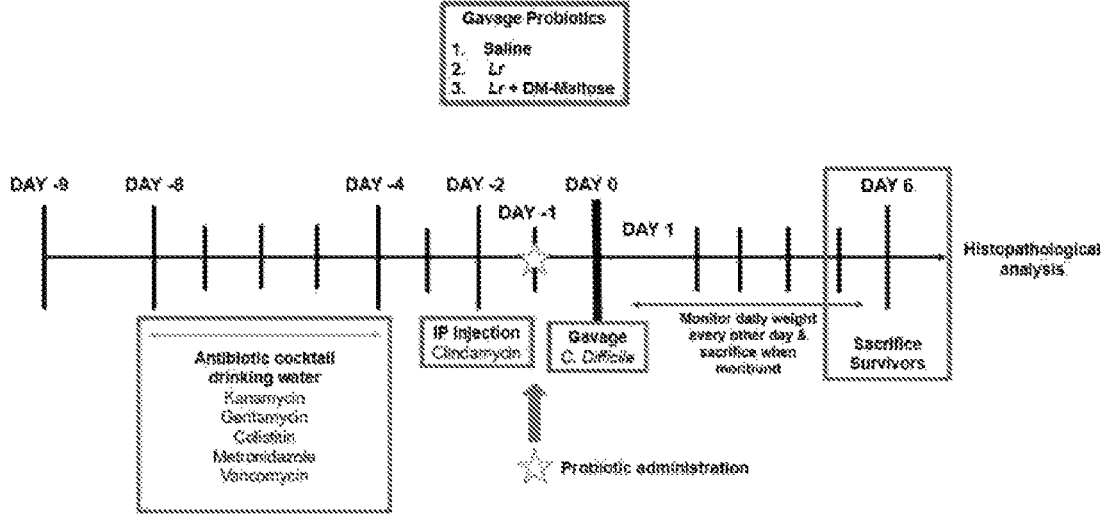

FIG. 7 shows the experimental model for CDI prophylaxis. The experimental model spans 15 days. Following randomization into control or treatment groups, mice to be subjected to the *C. difficile* protocol were provided an antibiotic cocktail in sterilized drinking water over 4 days (days −8 to −4). Two days after oral antibiotic administration, mice received a single IP injection of clindamycin (day −2). 24 hours after IP clindamycin, mice randomized to treatment groups received one dose of: (1) saline (2) planktonic (Lr), or (3) Lr+DM-maltose. A single gastric gavage dose of *C. difficile* was administered 24 hours after prophylactic treatment. Control mice received no antibiotics, no probiotics, and no *C. difficile*. Mice were observed for 6 days post treatment.

Figure 8:
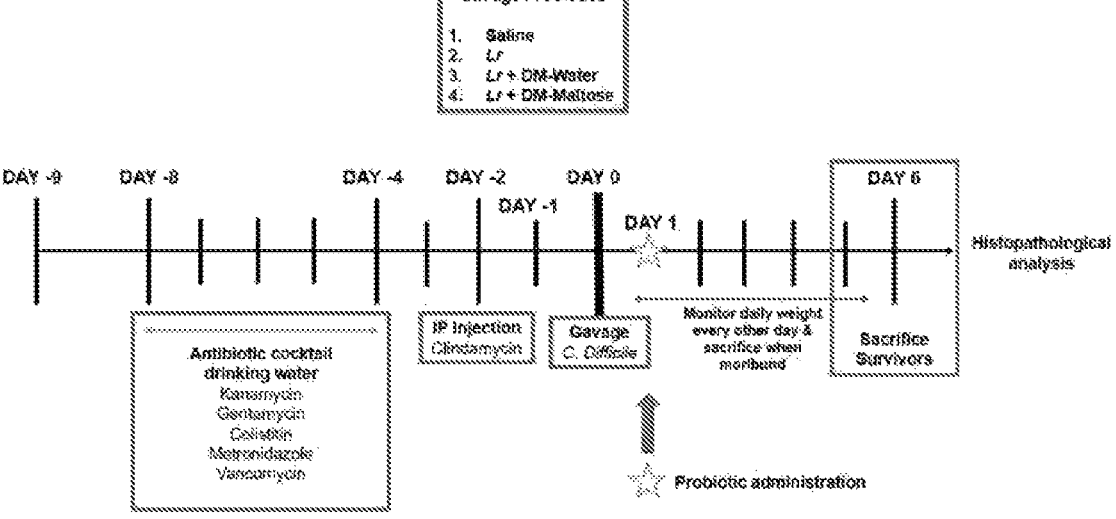

FIG. 8 shows an additional experimental model for CDI therapy. The experimental model spans 15 days. Following randomization into vehicle control and treatment groups, mice to be subjected to the *C. difficile* protocol were provided an antibiotic cocktail in sterilized drinking water over 4 days (days −8 to −4). Two days after oral antibiotic administration, mice received a single IP injection of clindamycin (day −2). 24 hours after the IP clindamycin, mice received a single dose of *C. difficile*. 24 h later, mice randomized to treatment groups received one dose of: (1) saline (2) planktonic Lr, (3) Lr+DM-water, or (4) Lr+DM-maltose. Control mice received no antibiotics, no *C. difficile* and no probiotics. Mice were observed for 6 days post *C. difficile* inoculation.

FIG. 9 shows clinical sickness scoring (CSS). Following *C. difficile* gavage, all mice were observed and assigned a daily Clinical Sickness Score. Clinical sickness scoring is based on three categories: stool scoring, behavior and weight loss. Each category is scored in a range, from a score of 0 indicating no signs of sickness to a score of 4 indicating maximum signs of sickness. Scores assigned in each category are added into one cumulative CSS for each mouse. Combined final scores for each mouse range from 0 to 12, with the total score recorded in the final analysis.

FIG. 10 shows histologic injury scoring (HIS). Mouse colon histology illustrating tissue damage in mice afflicted with *C. difficile* colitis. Scores in these categories range from no injury (0) to severe injury (3), and are combined into a cumulative HIS score ranging from 0 to 9. LU, lumen; LP, lamina propria, S, submucosa, thick arrow, level of mucosal injury; thin arrow, superficial epithelium injury.

Figure 11:
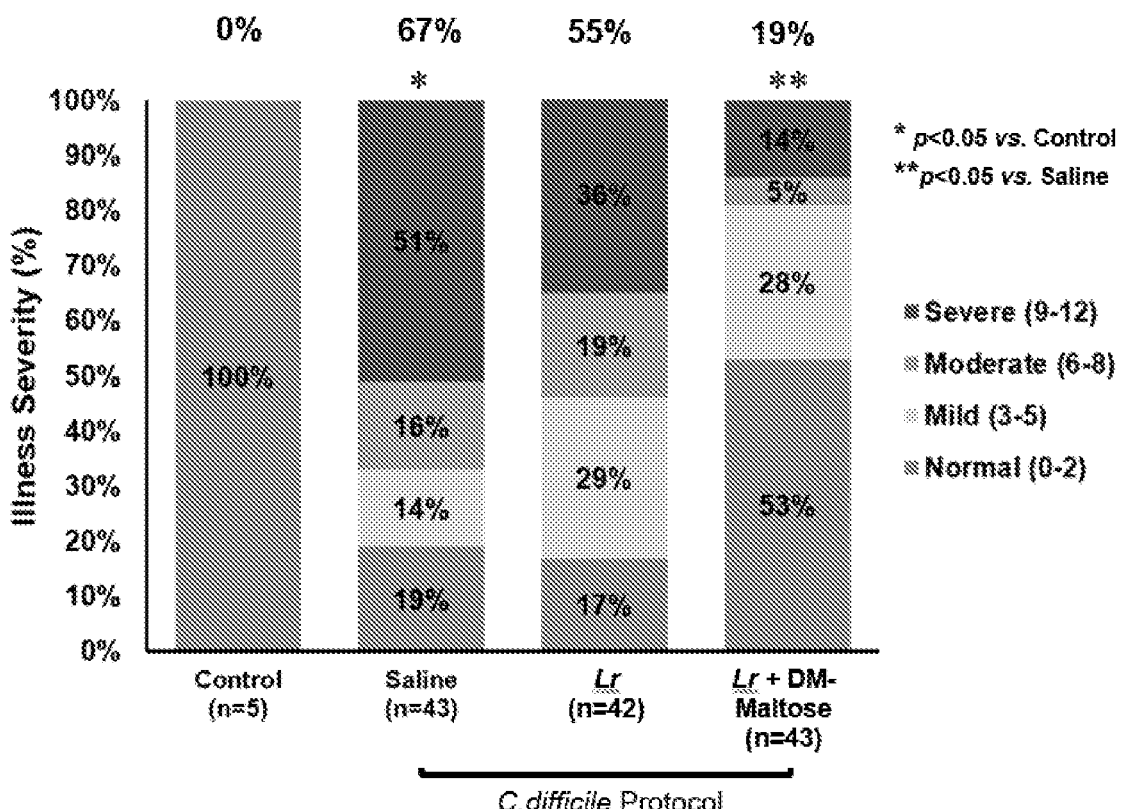

FIG. 11 shows clinical sickness score (CSS) grading for CDI prophylaxis. Control mice received no antibiotics, no probiotics, and no *C. difficile*. Mice subjected to the *C. difficile* protocol were randomized to receive one dose of: (1) saline (2) planktonic Lr, or (3) Lr+DM-maltose. Clinical sickness scores were assigned with daily observation. Total CCS for each animal ranges from 0 to 12 as illustrated in FIG. 10. Disease severity was categorized into four groups: normal (total score=0-2), mild (total score=3-5), moderate (total score=6-8), and severe (total score=9-12). Each shaded area reflects the percentage of animals in each CSS range. Scores≥6 are consistent with clinical *C. difficile* infection. The percentages at the top of each bar reflect severe+moderate CSS for each group.

Figure 12:
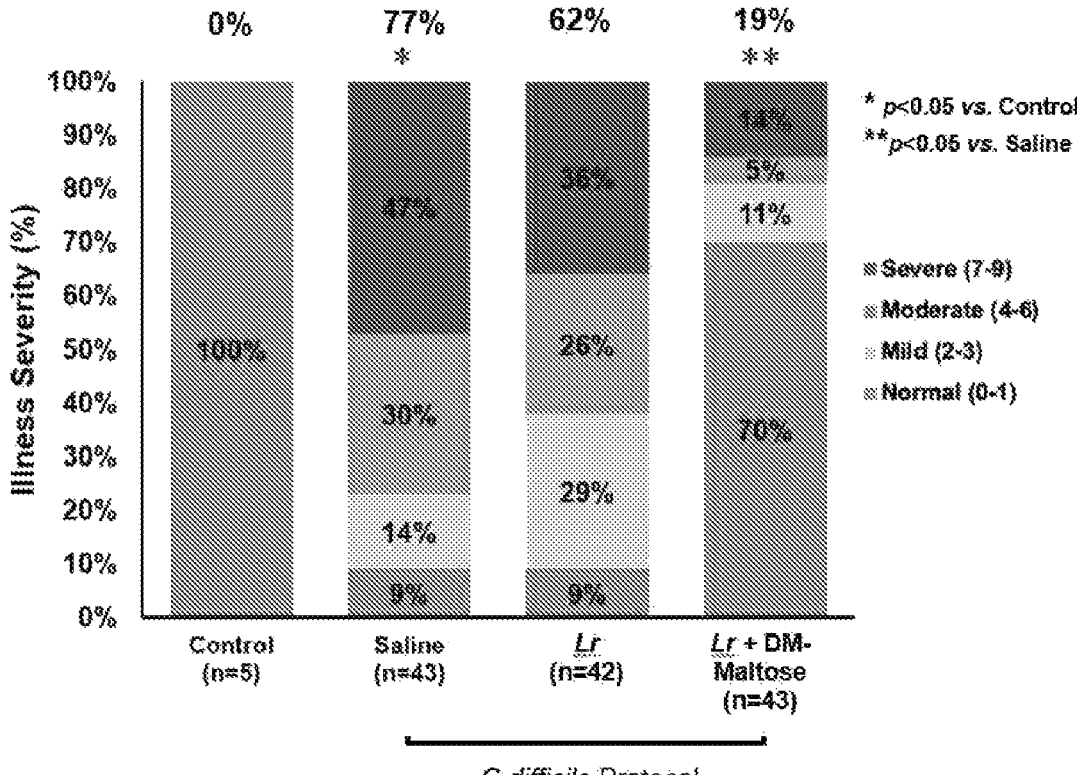

FIG. 12 shows histologic injury scores (HIS) grading for CDI prophylaxis. Control mice received no antibiotics, no probiotics, and no *C. difficile*. Mice subjected to the *C.*

*difficile* protocol were randomized to receive one dose of: (1) saline (2) planktonic Lr, or (3) Lr+DM-maltose. Total HIS for each animal ranges from 0 to 9 (illustrated in FIG. 11). Disease severity is categorized into four groups: normal (total score=0-1), mild (total score=2-3), moderate (total score=4-6), and severe (total score=7-9). Each colored area reflects the percentage of animals in each HIS range. Scores≥4 are consistent with histologic evidence of *C. difficile* infection. The percentages at the top of each bar reflect severe+moderate HIS for each group.

Figure 13:
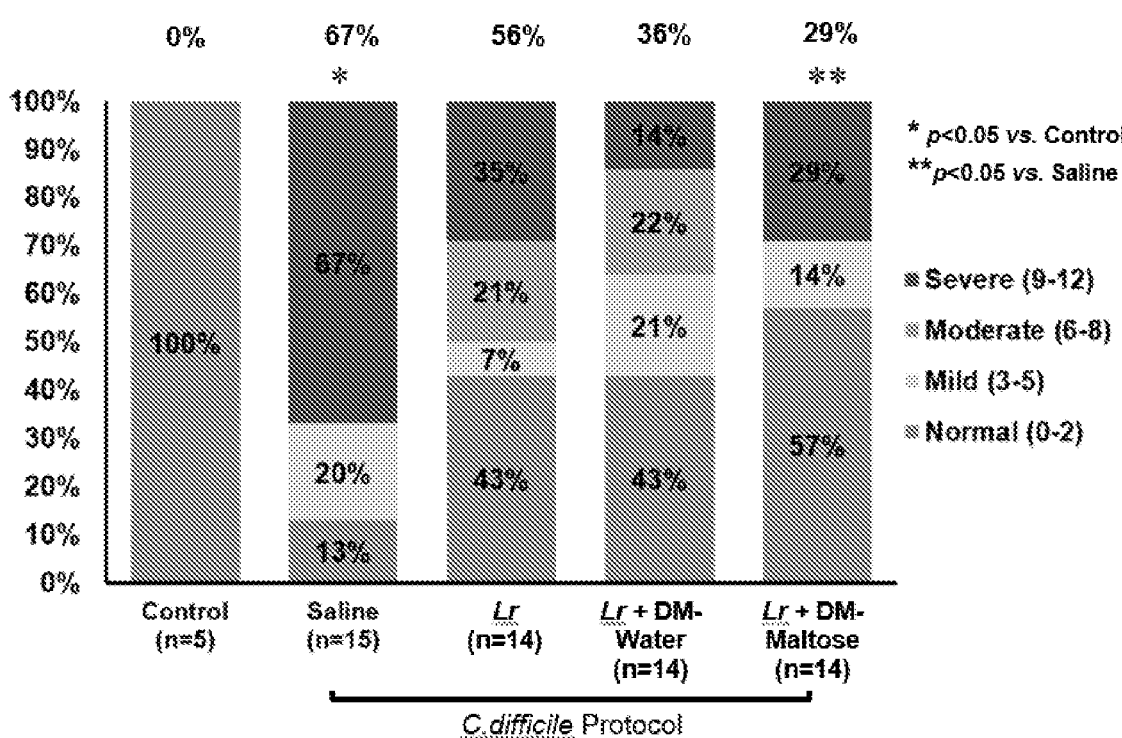

FIG. 13 is clinical sickness score (CSS) grading in CDI therapy. Control mice received no antibiotics, no *C. difficile* and no probiotics. Mice subjected to the *C. difficile* protocol were randomized to receive one dose of: (1) saline (2) planktonic Lr, (3) Lr+DM-water or (4) Lr+DM-maltose. Clinical sickness scores were assigned with daily observation. Total CCS for each animal ranges from 0 to 12 as illustrated in FIG. 10. Disease severity was categorized into four groups: normal (total score=0-2), mild (total score=3-5), moderate (total score=6-8), and severe (total score=9-12). Each colored area reflects the percentage of animals in each clinical sickness score range. Scores≥6 are consistent with clinical *C. difficile* infection. The percentages at the top of each bar reflect severe+moderate CSS for each group.

Figure 14:
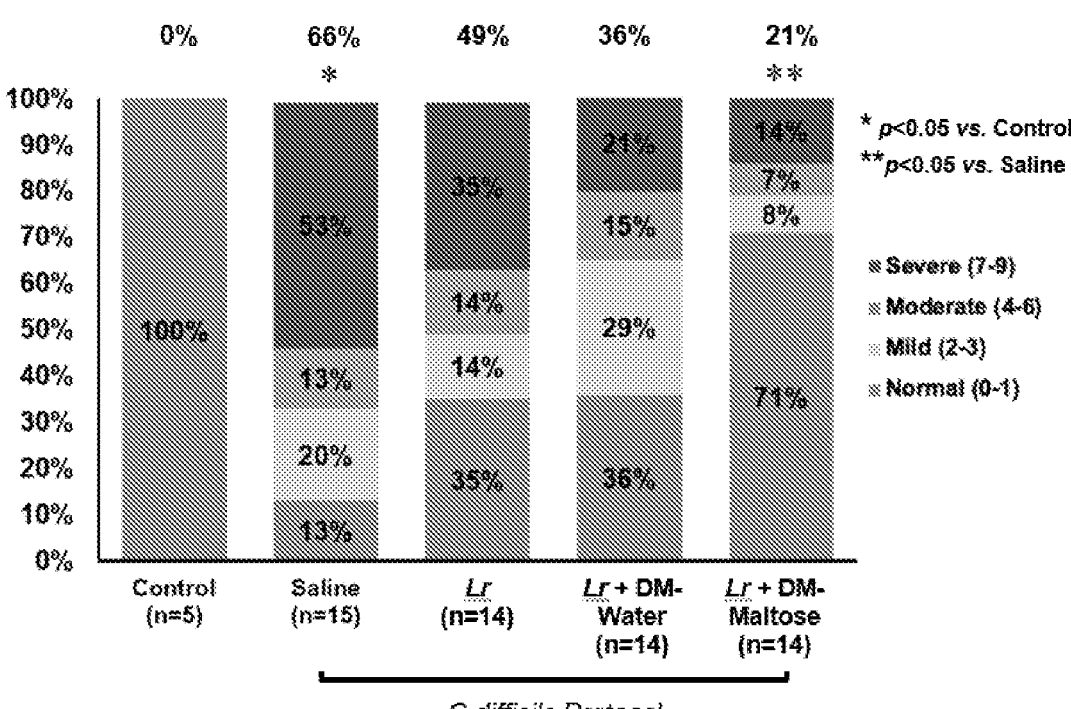

FIG. 14 shows istologic injury scores (HIS) grading in CDI therapy. Control mice received no antibiotics, no *C. difficile* and no probiotics. Mice subjected to the *C. difficile* protocol were randomized to receive one dose of: (1) saline (2) planktonic Lr, (3) Lr+DM-water or (4) Lr+DM-maltose). Total HIS for each animal ranges from 0 to 9 (illustrated in FIG. 11). Disease severity is categorized into four groups: normal (total score=0-1), mild (total score=2-3), moderate (total score=4-6), and severe (total score=7-9). Each colored area reflects the percentage of animals in each HIS range. Scores≥4 are consistent with histologic evidence of *C. difficile* infection. The percentages at the top of each bar reflect severe+moderate HIS for each group.

FIG. 15 shows FISH and immunofluorescence staining of epithelium, mucus, and bacteria in CDI model. Representative fluorescent images of bacteria from the epithelium for untreated (left panel), animals treated with antibiotics (middle panel) and animals treated with antibiotics and L-DM (right panel). Epithelium=blue (DAPI); mucus=green (UEA-1, Fucose); bacteria=red (EUB338, universal bacteria).

DETAILED DESCRIPTION

It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention.

The practice of the present technology will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a bacterium" includes a plurality of bacteria, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

A "biofilm" intends a thin layer or an organized community of microorganisms that at times can adhere to the surface of a structure, that may be organic or inorganic, together with the polymers, such as DNA, that they secrete and/or release. The biofilms are very resistant to microbiotics and antimicrobial agents. They live on gingival tissues, teeth, and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms.

A "prebiotic" intends a nutritional supplement for the probiotic bacterium. Prebiotics are food ingredients, for example, oligosaccharides, that are non-digestible by a subject (e.g., by a mammal such as a human), and that stimulates the growth or activity of one or more beneficial bacteria and/or inhibit the growth or activity of one or more pathogenic bacteria. A prebiotic may selectively stimulate the growth and/or activity of one or a limited number of bacteria in the subject.

A "prebiofilmic" intends a substance that supports biofilm formation and durability, for example the prebiofilmic can be a substance that supports the extracellular matrix of the biofilm like an eDNA binding polypeptide or protein or alternatively a substrate that can be converted into a substance that facilitate adhesion, e.g., sucrose. Non-limiting examples include DNABIII polypeptide or protein, maltose, and sucrose.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from *E. coli* strain U93 (HU), examples of which are provided in the attached sequence listing. Also intended are polypeptide fragments and equivalent polypeptides that have amino acid modifications that do not substantially change the biological activity of the protein or polypeptides, or active fragment thereof. Active fragments can include, for example, the c-terminal half or c-terminal third of the protein or polypeptide. Other DNA binding proteins that can be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813), as well as equivalent polypeptides and active fragments thereof.

A "microsphere" intends a porous and/or semi-permeable biofilm-carrying and/or compound-carrying (e.g., drug-carrying) particulate or granular material within the particular size range recited. As used herein, a microsphere consisting of particles 50 millimeters or less in diameter, and about 1 micron or more (e.g., about 1 to about 100 or alternatively, or alternatively, about 1 to about 75 microns, or alternatively about 1 to about 50, or alternatively about 1 to about 25, or alternatively about 1 to about 10 microns, or alternatively about 0.5 to about 200 microns, or alternatively about 0.5 to about 700 microns, or alternatively about 1 to about 600 microns, or alternatively less than about 700 microns, or alternatively less than about 600 microns, or alternatively less than 500 microns, or alternatively less than about 400 microns, or alternatively less than about 300 microns, or alternatively less than about 200 microns, or alternatively less than about 100 microns) in diameter. Non-limiting examples of such include hollow microspheres that are porous and/or semi-permeable, and can, in some aspects, contain a pharmaceutical or a drug, microcapsules, (in which the excipient forms a skin or shell that surrounds and contains a cargo, such as a drug, a chemical reductant, or absorptive or adsorptive molecules), and microparticles, which are used as a generic term for any particles in the recited size range, whether spherical or not, as those terms are typically used in the art. Table 1 provides non-limiting examples of microspheres that are commercially available and their characteristics. The microsphere diameters are described as having a wet or dry bead size. With respect to Sephadex beads, they are supplied in dry form (dry bead size) and swell in aqueous solutions. The particle size of Sephadex is usually reported in dry diameter, as the beads are swollen before use. Bead diameter can be determined using an optical light microscope according to British Standard 3406: Part 4, 1963 (as reported in Pereswetoff-Morath, et al. (1995) Int. J. Pharmaceutics 124:37-44).

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in E. coli are himA (Genbank accession No.: POA6X7.1) and himD (POA6Y1.1) genes. Non-limiting examples of such are provided in the attached sequence listing.

"HU" or "histone-like protein from E. coli strain U93" refers to a class of heterodimeric proteins typically associated with E. coli. HU proteins are known to bind DNA junctions. Related proteins have been isolated from other microorganisms. The complete amino acid sequence of E. coli HU was reported by Laine et al. (1980) Eur. J. Biochem.

TABLE 1

| | Dry bead size (μm) | | Wet bead size (μm) | | Permeability | Fractionation [Mr] globular | Fractionation [Mr] | Exclusion Limit | Swelling factor |
| --- | --- | --- | --- | --- | --- | --- | --- | --- | --- |
| Gel type | Low | High | Low | High | K* | proteins | dextrans | (Da) | (ml/g) |
| G-10 | 40 | 120 | 55 | 165 | 19 | 700 | 700 | >700 | 2-3 |
| G-15 | 40 | 120 | 60 | 180 | 18 | 1,500 | 1,500 | >1,500 | 2.5-3.5 |
| G-25 superfine | 10 | 40 | 17 | 70 | 9 | 1,000-5,000 | 100-100 | >5,000 | 4-6 |
| G-25 fine | 20 | 80 | 35 | 140 | 30 | 1,000-5,000 | 100-100 | >5,000 | 4-6 |
| G-25 medium | 50 | 150 | 85 | 260 | 80 | 1,000-5,000 | 100-100 | >5,000 | 4-6 |
| G-25 coarse | >100 | # | 87 | 510 | 290 | 1,000-5,000 | 100-5,000 | >5,000 | 4-6 |
| G-50 superfine | 20 | 50 | 20 | 80 | 13.5 | 1,000-30,000 | 500-10,000 | >30,000 | 9-11 |
| G-50 fine | 20 | 80 | 34 | 208 | 36 | 1,000-30,000 | 500-10,000 | >30,000 | 9-11 |
| G-50 coarse | 100 | 300 | 200 | 610 | 400 | 1,000-30,000 | 500-10,000 | >30,000 | 9-11 |
| G-75 superfine | 20 | 50 | 22 | 143 | # | 3,000-70,000 | 1,000-100,000 | >70,000 | 12-15 |
| G-75 | 40 | 120 | 90 | 280 | # | 3,000-80,000 | 1,000-50,000 | >70,000 | 12-15 |
| G-100 superfine | 10 | 40 | 25 | 100 | # | 4,000-100,000 | 1,000-100,000 | >100,000 | 15-20 |
| G-100 | 40 | 120 | 100 | 310 | # | 4,000-150,000 | 1,000-100,000 | >150,000 | 15-20 |

*Darcy's Law: $U = K (\Delta P) (L^{-1})$

U = linear flow rate in cm/h;

$\Delta P$ = pressure drop over bed in cm H20;

L = bed height in cm;

K = specific permeability constant of particle size and water regain not provided by manufacturer

A "biodegradable polymer" intends polymers that are biocompatible and can degrade in vivo by bodily processes to products that are readily disposable by the body and should not accumulate in the body.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, are preferentially used. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to microspheres made from materials which undergo bioabsorption in vivo over a period of time such that long term accumulation of the material in the patient is avoided. The biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the microspheres used in this invention.

103(3):447-481. Antibodies to the HU protein are commercially available from Abcam. Non-limiting examples of such are provided in the attached sequence listing.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "c-terminal polypeptide" intends the c-terminal half or c-terminal third of a polypeptide. As an example, for polypeptides containing 90 amino acids, the c-terminal polypeptide would comprise amino acids 46 through 90 or amino acids 60 through 90. In another aspect, the term intends the c-terminal 20 amino acids from the carboxy terminus.

A "n-terminal polypeptide" intends the n-terminal half of a polypeptide. As an example, for polypeptides containing 90 amino acids, the c-terminal polypeptide would comprise amino acids 1 through 45. In another aspect, the term intends the c-terminal 20 amino acids from the amino terminus.

The terms "polynucleotide" and "oligonucleotide" are used interchangeably and refer to a polymeric form of nucleotides of any length, either deoxyribonucleotides or ribonucleotides or analogs thereof. Polynucleotides can have any threedimensional structure and may perform any function, known or unknown. The following are nonlimiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by nonnucleotide components. A polynucleotide can be further modified after polymerization, such as by conjugation with a labeling component. The term also refers to both double and singlestranded molecules. Unless otherwise specified or required, any embodiment of this invention that is a polynucleotide encompasses both the doublestranded form and each of two complementary singlestranded forms known or predicted to make up the doublestranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides, antibodies and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

Glucotransferases are enzymes that establish glycosidic linkages. A non-limiting example of a sequence of the GTF protein is available at DSM 20016. gtfW ABQ83597.1 is provided at DSM 17938 gtfA WP_003671465. See also, Walter et al. (2008) Microbiology 154(Pt 1):72-80.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide, polynucleotide or nucleic acid, intends those having minimal homology while still maintaining desired structure or functionality. Unless specifically recited herein, it is contemplated that any nucleic acid, polynucleotide, polypeptide or protein mentioned herein also includes equivalents thereof. For example, an equivalent intends at least about 70%, or alternatively 80% homology or identity and alternatively, at least about 85%, or alternatively at least about 90%, or alternatively at least about 95%, or alternatively 98% percent homology or identity across the protein or a particular fragment thereof, and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "subject" or "patient" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder. In one aspect, the term "treatment" excludes "prevention."

To "prevent" intends to prevent a disorder or effect in vitro or in vivo in a system or subject that is predisposed to the disorder or effect. Examples of such is preventing the formation of a biofilm in a system that is infected with a microorganism known to produce one or alternatively, prevent a gastrointestinal disorder by supporting a healthy state of the patient's gut.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

*L. reuteri* is strain ATCC 23272 is commercially available from American Type Culture Collection. It was deposited as *Lactobacillus fermentum* Beijerinck, as strain F275 [DSM 20016]. The strain was described in Kandler et al. (1980) *Zentralbl. Bakteriol. Parasitenkd. Infektionskr. Hyg. Abt.* 1 *Orig.* C1:264-269 *and Int. J. Systematic Bacteriology* (1982) *Vol.* 32(2):266-268.

"Pharmaceutically acceptable carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

A "biocompatible scaffold" refers to a scaffold or matrix for with the ability to support biofilm proliferation upon administration to a subject. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. Nos. 6,638,369 and 8,815,276. In one aspect, the microsphere as described herein is a biocompatible scaffold.

"Administration" intends the delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and animals, treating veterinarian. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and the target cell or tissue. Non-limiting examples of route of administration include oral administration, vaginal, nasal administration (inhalation), injection, topical application and by suppository.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of a therapeutic composition, in some embodiments the effective amount is the amount sufficient to result in a protective response against a pathogen or alternatively to support a healthy state of being. In some embodiments, the amount is sufficient to accomplish one or more of 1) clear pathogen; 2) restore healthy microbiota; 3) modulate the immune system; 4) maintain metabolism and metabolic pathways; 5) reduce toxic compounds in the environment (toxic compounds in water, soil, air, and compounds such as heavy metals (e.g., chromium, arsenic, mercury, radioactive actinides, uranium, plutonium, thorium, polycyclic aromatic hydrocarbons (PAH), petroleum hydrocarbon, crude oil, refined oil, herbicide contamination or pesticide contamination); and 6) remediate a biofilm).

In the case of an in vitro or ex vivo applications, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent or composition of the present invention can be administered for therapy by any suitable route of administration. It will also be appreciated that the preferred route will vary with the condition and age of the recipient and the disease being treated.

Modes for Carrying Out the Disclosure

Microsphere Compositions

This methods of this disclosure comprise administration of a composition comprising, or alternatively consisting essentially of, or yet further consisting of, a microsphere, a biofilm-generating probiotic bacterium and a prebiotic, wherein the prebiotic comprises a nutritional supplementation for the probiotic bacterium. In one aspect, the composition further comprises one or more of: a biofilm, a pre-biofilmic, coating on the surface of the microsphere a therapeutic drug or agent, a chemical reductant, a molecule that promotes adsorption, a molecule that supports absorption. The microsphere comprises a solid core, a hollow core, wherein in one aspect, the microsphere encapsulates the prebiotic within the hollow core. The microsphere can be biocompatible and/or semi-permeable. In one aspect, the microsphere comprises a biofilm layer or coating on the external surface of the microsphere, that may be partially or completely covering the external surface of the microsphere. The microspheres in the composition can be the same or different in terms any parameter, e.g., composition and/or diameter and/or microbial loading.

Microsphere Components

In one aspect, the methods administer a biocompatible microsphere that comprises a material selected from the group of: a biodegradable polymer, a non-degradable polymer, a metal, and wherein the diameter of the microsphere is from about 0.5 microns to about 1000 microns. Additional preferred ranges are described herein and incorporated herein by reference. The microspheres can be porous and/or semi-permeable.

Non-limiting examples of biodegradable polymers are selected from one or more of: dextran; dextranomer; poly (lactic-co-glycolic acid) or PLGA; polycaprolactone or PLC; Chitosan; Gelatin; DNA hydrogen; acetalated dextran; poly(lactide); poly(glycolide); poly(lactide-co-glycolide); poly(lactic acid); poly(glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly (lactic acid-co-glycolic acid)/poly(ethylene glycol) copolymer; poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; Sephadex® copolymers and/or a combination thereof. In one aspect, the biodegradable polymer is or comprises Sephadex or Sephadex G-25.

Non-limiting examples of non-biodegradable polymers are selected from one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Non-limiting examples of polymers comprising the microsphere are selected from one or more of: Sephadex, Sephadex G-25, poly(lactic-co-glycolic acid)("PLGA"), polycaprolactone ("PLC"), chitosan; gelatin, DNA hydrogen; acetalated dextran, poly(lactide), poly(glycolide), poly (lactide-co-glycolide), poly(lactic acid), poly(glycolic acid), poly(lactic acid-co-glycolic acid), poly(lactide)/poly(ethylene glycol) copolymers, poly(glycolide)/poly(ethylene glycol) copolymer, poly(lactide-co-glycolide)/poly(ethylene glycol) copolymers, poly(lactic acid)/poly(ethylene glycol) copolymer, poly(glycolic acid)/poly(ethylene glycol) copolymer, poly(lactic acid-co-glycolic acid)/poly(ethylene glycol) copolymer, poly(caprolactone), poly(caprolactone)/ poly(ethylene glycol) copolymer, poly(orthoester), poly (phosphazene), poly(hydroxybutyrate), poly (hydroxybutyrate), poly(lactide-co-caprolactone); polycarbonate; polyesteramide; polyanhidride, poly(dioxanone), poly(alkylene alkylate), polyethylene glycol/ polyorthoester copolymer, polyurethane, poly(amino acid), polyetherester; polyacetal, polycyanoacrylate, poly(oxyethylene)/poly(oxypropylene) copolymer; and a combination thereof. In one aspect, the polymer is or comprises Sephadex or Sephadex G-25.

Non-limiting examples of metals include cobalt, chromium, gold, nickel, platinum, stainless steel, titanium, tantalum, nickel-titanium, an alloy, and combinations thereof.

Prebiotic

Non-limiting examples of the prebiotic of the composition comprise one or more of: a water-soluble carbohydrate, inulin, oligosaccharides, oligofructose, fructo-oligosaccharide, galacto-oligosaccharide, glucose, starch, maltose, maltodextrins, polydextrose, amylose, sucrose, fructose, lactose, isomaltulose, polyols, glycerol, carbonate, thiamine, choline, histidine, trehalos, nitrogen, sodium nitrate, ammonium nitrate, phosphorus, phosphate salts, hydroxyapatite, potassium, potash, sulfur, homopolysaccharide, heteropolysaccharide, cellulose, chitin, vitamins, and combination thereof.

In another aspect, the prebiotic is selected from one or more of trehalose; nitrogen such as in sodium nitrate, ammonium nitrate, phosphorus such in phosphate salts like hydroxyapatite, potassium such as in potash, sulfur, oligosaccharide, homopolysaccharide, heteropolysaccharide, cellulose, chitin, glucose, fructose, sucrose, maltose, starch, polydextrose, amylose, glycerol, carbonate, and combinations thereof. In one aspect, the prebiotic comprises or consists essentially of maltose.

In a yet further aspect, the prebiotic of the composition comprises one or more of vitamin mixtures to stimulate microbial growth, nitrogen such as in sodium nitrate, ammonium nitrate, phosphorus such in phosphate salts like hydroxyapatite, potassium such as in potash, sulfur, oligosaccharide, homopolysaccharide, heteropolysaccharide cellulose, chitin; glucose, fructose, sucrose, maltose, starch, polydextrose, amylose, glycerol, carbonate, and combinations thereof.

Probiotic Bacterium

In one aspect, the probiotic bacterium is selected to provide one or more of supporting anti-bacterial immunity, enhancing or supporting a healthy state in the subject enhancing or supporting the gastrointestinal barrier, or antagonizing disease-related bacterial infections. In another aspect, the probiotic bacterium is selected to prevent pathogen colonization and/or limit and/or clear the pathogen, and/or limit excessive inflammatory responses by down-regulating cytokine and chemokine production.

Non-limiting examples of the probiotic bacterium is one or more of *L. acidophilus, L. crispatus, L. gasseri*, group *L. delbrueckii, L. salivarius, L. casei, L. paracasei, L. planta-*

*rum, L. rhamnosus, L. reuteri,* (Lr), *L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles, Pseudomonas fluorescens, P. protegens, P. brassicacearum, P. aeruginosa; Azospirillum. brabrasilense, A. lipferum, A. halopraeferens, A. irakense; Acetobacter diazotrophicus; Herbaspirillum seropedicae; Bacillus subtilis, Pseudomonas stutzeri, fluorescens, P. putida, P. cepacian, P. vesicularis, P. paucimobilis; Bacillus cereus, B. thuringiensis, B. sphaericus; Shewanella oneidensis; Geobacter bemidjiensis, G. metallireducens, G. sulfurreducens, G. uraniireducens, G. lovleyi; Serratia marcescens, Desulfovibrio vulgaris, D. desulfuricans, Dechloromonas aromatic, Deinococcus radiodurans, Methylibium petroleiphilum, Alcanivorax borkumensis, Archaeglobus fulgidus, Haloferax* sp., *Halobacterium* sp., and combinations thereof. In one aspect, the probiotic is *L. reuteri.*

In another aspect, the probiotic is *L. reuteri* that produces GTF protein or containing the GTFW gene (available commercially from the American Type Culture Collection (ATCC 23272)).

Prebiofilmic

In other aspect, the prebiofilmic comprises an agent that supports biofilm formation and durability, non-limiting examples of such include a DNA binding polypeptide or protein and/or a DNABII polypeptide or protein or an equivalent of each thereof, optionally, a polypeptide comprising one or more of the attached sequence listing, or a biologically active fragment or equivalent of each thereof, alone or in combination. Additional prebiofilmics include maltose and sucrose.

Complimentary Agents

The microspheres and compositions containing the microspheres can further an agent, wherein the agent is selective against a pathogen that may compete with the probiotic organism. The complimentary agents can be in the core, on the surface of the microsphere in in the composition containing the microspheres. Non-limiting examples of such include chemical reductants; molecules and/or surfaces that promote adsorption (in core or on surface of microsphere); molecules and/or surfaces that promote absorption (in core or on surface of microsphere). In one aspect, the chemical reductants and molecules and/or surfaces that promote absorption are coated on the surface of the microsphere.

Biofilm Layer

In one aspect, the microsphere compositions further comprise a biofilm layer on the external surface of the microparticle. The layer can be from about 0.5 micron to about 1 millimeter in depth, and ranges in between, e.g., about 1 micron to about 500 microns, about 1 micron to about 250 microns, about 1 micron to about 200 microns, about 1 micron to about 100 microns, about 1 micron to about 50 microns, about 1 micron to about 40 microns, about 1 micron to about 30 microns, about 2 micron to about 100 microns, about 2 microns to about 50 microns, about 2 microns to about 40 microns, about 2 microns to about 30 microns, about 3 microns to about 100 microns, about 3 microns to about 50 microns, about 3 microns to about 40 microns, about 3 microns to about 30 microns, about 5 microns to about 100 microns, about 5 microns to about 50 microns, about 5 microns to about 40 microns, and about 5 microns to about 30 microns.

Compositions

The methods of this disclosure can in one aspect, administer one or a plurality of microsphere compositions as described herein (that may be the same or different from each other) in combination with a carrier, e.g., a pharmaceutically acceptable carrier or a biocompatible scaffold. Non-limiting examples pharmaceutically acceptable carriers include diluents, excipients or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Non-limiting examples of biocompatible scaffolds, include a scaffold or matrix for with the ability to support biofilm proliferation upon administration to a subject or an environment to be treated.

In one aspect, the compositions comprise a plurality of microspheres that are the same or different from each other, e.g., the same or different diameters, the same or different microsphere components, the same or different prebiotics, the same or different bacterial loading, the same or different diameter, the same or different bacterium, the same or different probiotics, the same or different complimentary agents, the same or different prebiofilmic, and hollow and/or solid cores.

The compositions can be formulated into dosage forms of the biofilm-generative probiotic bacterium, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be formulated or processed for ease of administration, storage and application, e.g., frozen, lyophilized, suspended (suspension formulation) or powdered; and processed as a suppository, tablet, solution, suspensions, pills, capsules, sustained release formulation.

Applications and Uses

Antibiotics induce dysbiosis leading to potential complications. One complication is *C. difficile* infection. Provided herein are methods for preventing or treating antibiotic induced dysbiosis in a patient in need thereof, comprising administering to the subject a composition comprising a microsphere, a biofilm-generating probiotic bacterium and a prebiotic, wherein the prebiotic comprises a nutritional supplementation for the probiotic bacterium, that is optionally administered prior to, concurrently or subsequent to administration of the antibiotic. In one aspect, the subject is immunocompromised, e.g., a patient undergoing chemotherapy.

Also provided herein is a method for preventing or treating *C difficile* infection caused by antibiotic induced dysbiosis in a patient in need thereof, comprising administering to the subject a composition comprising a microsphere, a biofilm-generating probiotic bacterium and a prebiotic, wherein the prebiotic comprises a nutritional supplementation for the probiotic bacterium, that is optionally administered prior to, concurrently or subsequent to administration of the antibiotic.

Further provided is a method for preventing or treating *C difficile* colitis in a patient in need thereof, comprising administering to the subject a composition comprising a microsphere, a biofilm-generating probiotic bacterium and a prebiotic, wherein the prebiotic comprises a nutritional supplementation for the probiotic bacterium.

The dosage and components of the composition will vary with the subject, the antibiotic and the health status of the patient. In one aspect, the composition is administered to provide from about $1\times10^7$ to about $1\times10^9$ CFU/ml of the biofilm-generating probiotic bacterium. The compositions can be formulated into dosage forms, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^7$ to about $1\times10^9$ CFU/ml, or about $1\times10^8$ CFU/ml.

The compositions can be administered at about 6, 12, 18, 24, 36, 48, and 72 hours, post- or pre-administration of the antibiotic, and can be administered in one or more doses.

The compositions can be administered orally, vaginally, topically, by inhalation, intravenously, intramuscularly, or by suppository. They can be administered in any suitable formulation.

This disclosure provides compositions use in the disclosed methods wherein the composition comprises a microsphere, a biofilm-generating probiotic bacterium and a prebiotic, wherein the prebiotic comprises a nutritional supplementation for the probiotic bacterium. In one aspect, the composition further comprises one or more of: a prebiofilmic, a biofilm layer, a therapeutic drug or agent. The microsphere comprises a solid core, a hollow core, wherein in one aspect, the microsphere encapsulates the prebiotic within the hollow core. In one aspect, the bacterium is Lr. and the prebiofilmic is sucrose and/or maltose.

In one aspect, the microsphere comprises a material selected from the group of: a biodegradable polymer, a non-degradable polymer, or a metal, and wherein the diameter of the microsphere is from about 0.5 microns to about 1000 microns, or alternatively rom about 0.5 microns to about 100 microns, or alternatively less than 100 microns.

Non-limiting examples of biodegradable polymers for medicinal use are selected from one or more of dextran, dextranomer, poly(lactic-co-glycolic acid) or PLGA, polycaprolactone or PLC, chitosan, gelatin, DNA hydrogen, acetalated dextran, poly(lactide), poly(glycolide), poly(lactide-co-glycolide), poly(lactic acid), poly(glycolic acid), poly(lactic acid-co-glycolic acid), poly(lactide)/poly(ethylene glycol) copolymers, poly(glycolide)/poly(ethylene glycol) copolymer, poly(lactide-co-glycolide)/poly(ethylene glycol) copolymers, poly(lactic acid)/poly(ethylene glycol) copolymer, poly(glycolic acid)/poly(ethylene glycol) copolymer, poly(lactic acid-co-glycolic acid)/poly(ethylene glycol) copolymer, poly(caprolactone), poly(caprolactone)/poly(ethylene glycol) copolymer, poly(orthoester), poly(phosphazene), poly(hydroxybutyrate), poly(hydroxybutyrate), poly(lactide-co-caprolactone), polycarbonate, polyesteramide; polyanhidride, poly(dioxanone), poly(alkylene alkylate), polyethylene glycol/polyorthoester copolymer, polyurethane, poly(amino acid), polyetherester, polyacetal, polycyanoacrylate, poly(oxyethylene)/poly(oxypropylene) copolymer, Sephadex® copolymers and/or a combination thereof.

Non-limiting examples of non-biodegradable polymers for medicinal use are selected from one or more of poly (ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly (ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

Non-limiting examples of metals include cobalt, chromium, gold, nickel, platinum, stainless steel, titanium, tantalum, nickel-titanium, an alloy, and combinations thereof.

Non-limiting examples of the prebiotic of the composition for medicinal use comprises one or more of a water-soluble carbohydrate, inulin, oligofructose, fructo-oligosaccharide, galacto-oligosaccharide, glucose, maltose, maltodextrins, polydextrose, sucrose, fructose, lactose, isomaltulose, polyols, glycerol, thiamine, choline, histidine, and combination thereof.

Non-limiting examples of the probiotic bacterium is one or more of *L. acidophilus, L. crispatus, L. gasseri,* group *L. delbrueckii, L. sahvarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles,* and combinations thereof.

Non-limiting examples of the prebiofilmic comprises an agent that supports biofilm formation and durability, non-limiting examples of such include a DNA binding polypeptide or protein and/or a DNABII polypeptide or protein or an equivalent of each thereof, optionally, a polypeptide comprising one or more of the attached sequence listing, or a biologically active fragment or equivalent of each thereof, alone or in combination. Other examples include maltose and sucrose.

The microspheres and compositions containing the microspheres can further an agent, wherein the agent is selective against a pathogen that may compete with the probiotic organism.

The complimentary agents can be in the core, on the surface of the microsphere in in the composition containing the microspheres.

In a further aspect, the microsphere further comprises a biofilm layer that partially or fully surrounds the microsphere.

This compositions for medicinal use can be provide as a composition, comprising one or a plurality of microsphere compositions as described herein in combination with a carrier, e.g., a pharmaceutically acceptable carrier or a biocompatible scaffold.

In one aspect, the compositions comprise a plurality of microspheres that are the same or different from each other, e.g., the same or different diameters, the same or different microsphere components, the same or different biofilm layer, the same or different probiotics, the same or different complimentary agents, the same or different prebiofilmic, and hollow and/or solid cores.

The compositions can be formulated into dosage forms of the biofilm-generative probiotic bacterium, e.g., or provide from an effective amount of the microsphere composition for the end use, e.g., from about $1\times10^5$ to $1\times10^{11}$ CFU/ml, or alternatively from about $1\times10^5$ to about $1\times10^{10}$ CFU/ml, or about $1\times10^5$ to about $1\times10^9$ CFU/ml, or about $1\times10^6$ to about $1\times10^{11}$ CFU/ml, or about $1\times10^6$ to about $1\times10^9$ CFU/ml, or about $1\times10^7$ to about $1\times10^{11}$ CFU/ml, or about $1\times10^7$ to about $1\times10^{10}$ CFU/ml, or about $1\times10^{7}$ to about $1\times10^{9}$ CFU/ml, or about $1\times10^{8}$ CFU/ml.

The compositions are useful for the treatment of a mammal such as a human, simians, murines, such as, rats, mice, chinchilla, canine, such as dogs, leporids, such as rabbits, livestock, sport animals and pets. The mammal can be selected from the group of an adult, a juvenile, an infant or a fetus.

One can determine if the treatment has been successful by monitoring for a reduction in disease symptoms and by assaying or assaying for the presence of a probiotic culture in the subject.

The biofilm-generating probiotic bacterium adheres to the surface of the biocompatible microsphere and generates a biofilm. The biocompatible microsphere has either a solid or hollow core. When the biocompatible microsphere has a hollow core, it can carry a prebiotic and any nutritional supplementation for the probiotic bacterium as a cargo. It one aspect, for a microsphere with a hollow core, the sphere surface can be semi-permeable (porous) to allow cargo to diffuse to the bound bacteria at high localized concentrations or it can be impermeable but slowly degrade to allow the contents to be released. The prebiotic can be encapsulated within the hollow core. The microsphere can also carry a drug, or a compound, or an agent, which is selective against the growth or proliferation of a pathogen. In addition to a biocompatible microsphere, biofilm-generating probiotic and prebiotic, a novel probiotic formulation may also contain a prebiofilmic, which a substance that supports biofilm formation and durability, specifically, the prebiofilmic is a DNA binding polypeptide or protein and/or a DNABII polypeptide or protein, a fragment and/or an equivalent of each thereof. Non-limiting examples of such are provided in the attached sequence listing. One or more drug, compound or agent as well as one or more prebiofilmic can be within a single microsphere.

The prebiotic can support the growth of any probiotic bacteria, including biofilm-generating bacteria. The prebiotic is usually one or more of a water-soluble carbohydrate, such as inulin, oligofructose, fructo-oligosaccharide, galacto-oligosaccharide, glucose, maltose, maltodextrins, polydextrose, sucrose, fructose, lactose, isomaltulose, polyols, and glycerol. The combination of various prebiotics can be used to support the growth of probiotics.

Probiotics are any type of micro-organisms that have health benefits. Probiotics are also commonly consumed as part of fermented foods with specially added active live cultures, such as in yogurt, soy yogurt, or as dietary supplements. Probiotics can also be taken as a suppository. Some limiting examples of probiotics are *L. acidophilus, L. crispatus, L. gasseri*, group *L. delbrueckii, L. sahvarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum*, and *S. thermophiles*. In one aspect, the probiotic is an *L. reuteri* that expresses GTF protein. All strains of *L. reuteri* possess at least one GTF protein, although they can vary between strains, e.g., in DSM20016, the GTF is GTFW and uses maltose as its sole substrate while in DSM 17938 the GTF is GTFA, and it uses sucrose as its sole substrate.

Probiotics support anti-bacterial immunity by preventing pathogen colonization and/or limiting excessive inflammatory responses. Without being bound by theory, the probiotics down-regulate cytokine and chemokine production.

The biocompatible microsphere can be one or more of a biodegradable polymer, a non-biodegradable polymer, a metal, or a mixture thereof. The biodegradable polymer can be selected from, but not limited to: dextran; dextranomoer; poly(lactic-co-glycolic acid) or PLGA; polycaprolactone or PLC; Chitosan; Gelatin; DNA hydrogen; acetalated dextran; poly(lactide); poly(glycolide); poly(lactide-co-glycolide); poly(lactic acid); poly(glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly (lactic acid-co-glycolic acid)/poly(ethylene glycol) copolymer; poly(caprolactone); poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; Sephadex® copolymers (made from dextran cross-linked with epicholorhydine, commercially available from Sigma-Aldrich and noted in Koo and Wankat (1988) Korean Biochem. J. 21(1)) and/or a combination thereof. The non-biodegradable polymer can be selected from, but not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly (vinyl imidazole), chorosulphonated polyolefins, polyethylene oxide, and copolymers and blends thereof. The metal can be selected from, but not limited to, cobalt, chromium, gold, nickel, platinum, stainless steel, titanium, tantalum, nickel-titanium, and alloys and combinations thereof.

The microspheres are selected to facilitate the endurance and robustness of the probiotic biofilms are identified and characterized. It has been shown that probiotic biofilms formed on the biodegradable (and FDA approved) surface, poly (lactic-co-glycolic acid) (PLGA) yields biofilms that are superior at preventing pathogen translocation through the epithelial barrier. Other FDA approved or generally regarded as safe (GRAS) materials that can be used to create surfaces to grow biofilms are also examined. The results using biological effectiveness and durability in animal models and shelf life as the base criteria are prioritized. Finally, to further improve the effectiveness of the introduction and maintenance of the probiotic biofilm, prebiotic substances to the probiotic biofilm surface by way of diffusible cargo within the microspheres are provided.

In a further aspect, the microspheres are partially or fully coated by a biofilm layer. The layer can be from about 0.5 micron to about 1 millimeter in depth, and ranges in between, e.g., about 1 micron to about 500 microns, about 1 micron to about 250 microns, about 1 micron to about 200 microns, about 1 micron to about 100 microns, about 1 micron to about 50 microns, about 1 micron to about 40 microns, about 1 micron to about 30 microns, about 2 micron to about 100 microns, about 2 microns to about 50 microns, about 2 microns to about 40 microns, about 2 microns to about 30 microns, about 3 microns to about 100 microns, about 3 microns to about 50 microns, about 3 microns to about 40 microns, about 3 microns to about 30 microns, about 5 microns to about 100 microns, about 5 microns to about 50 microns, about 5 microns to about 40 microns, and about 5 microns to about 30 microns.

In another aspect, the composition for use in the methods comprise, or alternatively consist essentially of, or yet further consist of, a biocompatible microsphere, a biofilm-generating probiotic bacterium and a prebiotic, wherein the prebiotic comprises, or alternatively consists essentially of, or yet further consists of a nutritional food source or supplement for the culturing and/or growth of the probiotic bacterium. The composition can further comprise a prebiofilmic. The prebiofilmic comprises a substance that supports biofilm formation and durability, specifically; the prebiofilmic can be a DNA binding polypeptide or protein and/or a DNABII polypeptide or protein. In one aspect, the composition is frozen, for example flash frozen. In another aspect, the composition is lyophilized or dried in powder form. In a further aspect, it is formulated for administration as a suppository or in ingestible form (e.g., tablet). The composition can further comprise a mixture of the above-noted microspheres, e.g., a mixture containing two or more probiotic bacterium and/or two or prebiofilmics and/or two or more nutritional and/or supplement to support the culturing and/or growth of the probiotic bacterium.

In some embodiments, the prebiotic comprises a water-soluble carbohydrate selected from, but not limited to, one or more of inulin, oligofructose, fructo-oligosaccharide, galacto-oligosaccharide, glucose, maltose, maltodextrins, polydextrose, sucrose, fructose, lactose, isomaltulose, polyols, glycerol, and combinations thereof. In one aspect, the composition further comprises a solid or a liquid carrier, such as a pharmaceutically acceptable carrier.

As is apparent to those of skill in the art, the prebiotic and prebiofilmic are selected in each composition to specifically support the growth of the probiotic bacterium. By way of example only, when the probiotic bacterium comprises L. reuteri, the composition comprises an effective amount of one or more of maltose, sucrose, glycerol and optionally HU polypeptide or protein, to support the growth and maintenance of the probiotic when administered to the subject or patient. Non-limiting examples of prebioflimic compositions include, without limitation, one or more of the polypeptides provided in the attached sequence listing, a c-terminal fragment thereof, or a n-terminal fragment thereof, or the additional strains and polypeptides and fragments thereof, such as the full length or the c-terminal fragment or the n-terminal fragment of the protein, and equivalents of each thereof. Additional nutritional supplements for the support of other probiotic bacterium are disclosed in Bergey's Manual of Determinative Bacteriology, 9$^{th}$ Ed, Ed. Holt et al., WilliamsWilkins (1994), Non-limiting examples of a probiotic bacterium for use in the composition includes, without limitation, one or more of L. acidophilus, L. crispatus, L. gasseri, group L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles, or a combination thereof. As is apparent to those of skill in the art, one or more bacterium can be combined in a single composition. In some embodiments, the probiotic bacterium is Lactobacillus reuteri that in a further aspect, expresses GTF protein. In other aspects, it express GTFA protein. The bacteria are available from commercial sources, such as the American Type Culture Collection (ATCC). In one aspect, the one or more probiotic bacterium in the composition supports anti-bacterial immunity. In other aspects, the one or more probiotic bacterium in the composition prevents pathogen colonization and/or limits excessive inflammatory responses by down-regulating cytokine and chemokine production. In some embodiments, the composition further comprises an agent, and the agent is selective against a pathogen, such as a competing pathogen.

The biocompatible microsphere comprises one or more of a biodegradable polymer, a non-biodegradable polymer, a metal, or a combination thereof. In some embodiments, the microsphere comprises a solid core. In some embodiments, the microsphere comprises a hollow core. In some embodiments, the prebiotic is encapsulated within the hollow core of the microsphere and can be released at high concentrations to just the adhered probiotic either due to the semipermeable nature of the microsphere surface or via the gradual degradation of the microsphere.

In one aspect, the methods administer a composition comprising, or alternatively consisting essentially of, or yet further consisting of, a PGLA-biocompatible microsphere, one or more biofilm-generating probiotic bacterium, and a nutritional supplementation comprising one or more of sucrose, maltose or glycerol in an amount to support the growth of the probiotic bacterium. The biofilm-generating probiotic bacterium may comprise Lactobacillus reuteri ("L. reuteri or Lr"), that can optionally express GTF protein. The composition may further comprise, or alternatively consist essentially of, or yet further consist of, an effective amount of IHF or HU polypeptide or protein. The composition can further comprise a pharmaceutically acceptable carrier or a biocompatible scaffold and is optionally formulated as a suppository.

In one aspect, the methods administer a composition comprising, or alternatively consisting essentially of, or yet further consisting of, a Sephadex or Sephadex G-25 biocompatible microsphere, one or more biofilm-generating probiotic bacterium for example L. reuteri, and a nutritional supplementation comprising maltose in an amount to support the growth of the probiotic bacterium. The biofilm-generating probiotic bacterium may comprise Lactobacillus reuteri ("L. reuteri or Lr"), that can optionally express GTF protein. The composition may further comprise, or alternatively consist essentially of, or yet further consist of, an effective amount of IHF or HU polypeptide or protein. The composition can further comprise a pharmaceutically acceptable carrier or a biocompatible scaffold and is optionally formulated as a suppository.

The size of the microsphere can range from about 0.5 microns to about 100 microns. In certain embodiments, the microsphere is less than about 100 microns in diameter. In other embodiments, the microsphere is less than about 50 microns, or less than about 40 microns, or less than about 30 microns, less than about 20 microns, less than about 10 microns, or less than about 5 microns, or less than 3 microns to 0.5 microns in diameter. In further embodiments, the microsphere is from about 0.5 microns to about 90 microns, or to about 80 microns, or to about 70 microns, or to about 60 microns, or to about 50 microns, or to about 40 microns, or to about 30 microns, or to about 20 microns, or about 10 microns, or about 5 microns, or about 3 microns, or about 2 microns, or about 1 micron, in diameter. Alternatively, the diameter is from about 1 to about 100, or alternatively from about 1 to about 75, or alternatively from about 1 to about 50, or alternatively from about 1 to about 25, or alternatively from about 1 to about 15, or alternatively from about 1 to about 10, microns in diameter.

In some embodiments, the microsphere is a biodegradable polymer, non-limiting examples of such include: dextran, dextranomer; poly(lactic-co-glycolic acid)("PLGA"); polycaprolactone ("PLC"); chitosan; gelatin; DNA hydrogen;

acetalated dextran; poly(lactide); poly(glycolide); poly(lactide-co-glycolide); poly(lactic acid); poly(glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly(lactic acid-co-glycolic acid)/poly(ethylene glycol) copolymer; poly(caprolactone); poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; and combinations thereof. In some embodiments, the biodegradable polymer is poly(lactic-co-glycolic acid) or PLGA.

In some embodiments, the microsphere comprises a non-biodegradable polymer. Non-limiting examples of non-biodegradable polymers, include without limitation, of one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

In some embodiments, the microsphere comprises a metal. The metal can be selected from, but not limited to, one or more of cobalt, chromium, gold, nickel, platinum, stainless steel, titanium, tantalum, nickel-titanium, and alloys and combinations thereof.

Pharmaceutical Compositions

The composition for use in the methods can be formulated as a frozen composition, e.g., flash frozen, dried or lyophilized for storage and/or transport. In addition, the composition can be administered alone or in combination with a carrier, such as a pharmaceutically acceptable carrier or a biocompatible scaffold. Compositions can be conventionally administered rectally as a suppository, parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suppositories, suspensions, tablets, pills, capsules, sustained release formulations or powders and contain about 10% to about 95% of active ingredient, preferably about 25% to about 70%.

Typically, compositions are administered in a manner compatible with the dosage formulation, and in such amount as will be therapeutically effective for the disease or condition by treated. The quantity to be administered depends on the subject to be treated. Precise amounts of the composition to be administered depend on the judgment of the practitioner. Suitable regimes for initial administration and boosters are also variable, but are typified by an initial administration followed by subsequent administrations.

In many instances, it will be desirable to have multiple administrations of the compositions about, at most about or at least about 3, 4, 5, 6, 7, 8, 9, 10 days or more. The administrations will normally range from 2 day to twelve week intervals, more usually from one to two week intervals. Periodic boosters at intervals of 0.5-5 years, usually two years, may be desirable to maintain the condition of the immune system In some embodiments, additional pharmaceutical compositions are administered to a subject to support or augment the compositions as described herein. Different aspects of the present invention involve administering an effective amount of the composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The carrier may be a solvent or dispersion medium containing, for example, water, ethanol, polyol (for example, glycerol, propylene glycol, and liquid poly(ethylene glycol), and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of undesirable microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Processes for Preparing Compositions

To prepare a composition as described herein, a biocompatible microsphere is admixed with a biofilm-generating probiotic bacterium and a prebiotic. In one aspect, the method further comprises adding or admixing a prebiofilmic that supports the formation and growth of a biofilm by the bacterium. Non-limiting examples of such include, one or more of maltose, dextrose, a DNA binding polypeptide or protein and/or a DNABII polypeptide or protein. In a further aspect, the microspheres are contacted with a biofilm or placed into a culture that supports the growth of a biofilm on the surface of the microsphere. Additional components, as disclosed herein, can be further admixed with the microspheres, etc.

The compositions can be formulated or processed for ease of administration, storage and application, e.g., frozen, lyophilized, suspended (suspension formulation) or powdered; and processed as a suppository, tablet, solution, suspensions, pills, capsules, sustained release formulation.

In one aspect, the composition is prepared as a static culture of L. reuteri (purchased from the American Type Culture Collection (ATCC 23272); grown in De Man, Rogosa and Sharpe (MRS) medium at 37° C. under anaerobic conditions (5% $H_2$, 10% $CO_2$, 85% $N_2$). After growth, the L. reuteri culture is pelleted at 4,000×g for 2 min, the supernatant removed, the cell pellet washed three times with sterile saline, and the bacteria resuspended in one volume of sterile saline. The DM-maltose component is prepared by weighing dry Sephadex G25 Superfine microspheres, autoclaving to sterilize, and making a 25% w/v suspension with 1M maltose solution (filter sterilized). The slurry is incubated at RT overnight to allow total absorption of the maltose into the DM. The L. reuteri and DM-maltose slurry are incubated together at RT for 30 min prior to use. The final dose per administration of DM-maltose is $2×10^8$ CFU L. reuteri and 1 mg of DM.

This disclosure also provides a lyophilized form microspheres comprising a probiotic bacterium such as for example, L. reuteri. L. reuteri is grown and removed from the MRS growth medium as disclosed above but is resuspended into one tenth volume cryoprotectant (10% maltose solution) to account for viability loss during the freeze-drying process. The bacteria are the flash-frozen in a dry ice/ethanol bath for 30 min then transferred to a Labconco Freezone 2.5 L lyophilizer for 24 h at −50° C. and 0.05 mbar. The lyophilized L. reuteri are stored in the dark at 4° C. For administration, the lyophilized bacteria are rehydrated in sterile saline, diluted to $2×10^9$ CFU/ml, and added to a slurry of DM-maltose that is prepared as above. The mixture is incubated at RT for 30 min prior to use. In one aspect the dose per administration of the reconstituted DM-microsphere is $2×10^8$ CFU L. reuteri and 1 mg of DM.

To assess the impact of lyophilization and storage on L. reuteri viability, $2×10^{10}$ CFU of L. reuteri 23272 was lyophilized and aliquots were placed in the dark at −20° C., 4° C., and 22° C. for ten months. Each month, samples were rehydrated with saline and assessed for viability using plate counts. This study demonstrated that colder temperatures were better for preserving L. reuteri (see FIG. 1B).

EXPERIMENTAL

Experiment No. 1

Background

Probiotics are defined as live nonpathogenic bacteria that confer a health benefit to the host. Ollech et al. (2016) Best Pract Res Clin Gastroenterol 30(1): 111-118. Prevention and treatment strategies have utilized probiotics in an attempt to restore normalcy to the intestinal microbiome. McFarland et al. (2015) Antibiotics 4(2):160-178. CDI most commonly occurs after the administration of antibiotics, which disturb the intestinal microbiome, allowing C. difficile to predominate. Evans et al. (2015) Clin Infect Dis. 60 (suppl_2): S66-S71. Ollech et al. (2016) Best Pract Res Clin Gastroenterol 30(1): 111-118. Crow et al. (2015) Pharmacother J Hum Pharmacol Drug Ther. 35(11):1016-1025. Several clinical studies suggest that probiotics may be useful as adjunctive therapies and may prevent CDI. Spinier et al. (2016) Anaerobe 41:51-57. McFarland et al. (2018) J Hosp Infect. 99(4):443-452. Shen et al. (2017) Gastroenterology. 152(8):1889-1900. However, there has been no general consensus on the type of probiotic used or how to best administer the probiotics. McFarland et al. (2018) J Hosp Infect. 99(4):443-452. Crow et al. (2015) Pharmacother J Hum Pharmacol Drug Ther. 35(11):1016-1025. Additionally, there remains the question as to how the probiotic would survive the acidity of the stomach when given orally to produce effects in the lower GI tract.

Applicants investigated the use of Lr in the context of a biofilm as part of a microparticle delivery system to protect the intestines from CDI in a mouse model. Lr are briefly incubated with biocompatible, biodegradable dextranomer microspheres (DM) to produce a biofilm. DM are porous spheres composed of cross-linked polysaccharides of glucose or glucan that range from ~20 to 600 μm in diameter. Sold under various brand names, their current applications include size exclusion chromatography (Sephadex®) as well as FDA-approved medical treatments including an injectable bulking gel for fecal incontinence (Solesta®), an injectable bulking gel for vesicoureteral reflux (Deflux®), and wound dressings (Debrisan®). Supplied as a dry powder, the porous structure of DM allows for it to carry diffusible cargo when hydrated, thus the microspheres can act as carriers for various compounds. Navarro et al. (2017) Front Microbiol. 8:489.

Treatment

Lr biofilm production Lr was incubated with DM loaded with either sucrose or maltose leading to increased biofilm formation in as little as 5 minutes.

Establishment of an improved model of antibiotic-associated murine CDI Applicants utilized a reliable murine model of antibiotic-associated experimental CDI in which a cocktail of oral antibiotics (kanamycin, gentamycin, colistin, metronidazole, vancomycin) are administered over a 4-day period, followed by an IP dose of clindamycin and gastric gavage of C. difficile ($1.5×10^7$ CFU). Standardized clinical sickness score and histological injury score grading systems were developed by Applicants. Clinical sickness scores are determined based on stool appearance, behavior and weight loss (Table 2). After sacrifice, mouse colons are harvested, fixed in formalin, H&E stained, histologic sections are prepared, and the sections are graded blindly for histologic injury. Histological injury scores are based on epithelial tissue damage, mucosal edema, and neutrophil infiltration.

TABLE 2

| Modified Bristol stool scoring | | Behavior | | Weight loss | |
|---|---|---|---|---|---|
| 0 | Sausage shaped, lumpy or with cracks on surface | 0 | Able to ambulate, normal posture, eyes open, explores cage freely | 0 | ≥100% original weight |
| 1 | Sausage/snake-like, smooth & soft texture | 1 | Sluggish ambulation & hunched posture, still moving around cage | 1 | 96-99% original weight |
| 2 | Soft blobs or fluffy pieces, easily passable | 2 | Sluggish ambulation, hunched posture, little spontaneous ambulation | 2 | 91-95% original weight |
| 3 | Entirely liquid stool | 3 | Only ambulates with stimulation, hunched posture, eyes closed | 3 | 86-90% original weight |
| 4 | Mucous stool | 4 | Unable to ambulate, hunched posture, eyes closed, unresponsive or dead | 4 | ≤85% original weight |

Table 2 Clinical Sickness Score (CSS) grading. Shown are clinical signs of sickness indicative of *C. difficile* infection. The CSS is composed of three categories (stool appearance, behavior and weight loss), with scores in each subcategory ranging from 0 (no signs of sickness) to 4 (maximum signs of sickness) in each. Scores are combined into a cumulative CSS score for each mouse that ranges from 0 to 12. Mice are scored daily following *C. difficile* gavage, and their highest scores are recorded for data analysis.

Effect of Lr in our animal model of antibiotic-associated *C. difficile* colitis. Using this murine model, Applicants demonstrated that Lr administered in its biofilm state prior to inoculation with *C. difficile* protects the intestines from injury. Mice were subjected to the described experimental model of CDI and randomized to one of the following groups: (1) no treatment (vehicle control); (2) planktonic Lr; (3) Lr+DM (empty microspheres), or (4) Lr+DM-maltose (microspheres loaded with maltose to increase biofilm formation). Administration of Lr+DM-maltose resulted in significantly improved clinical sickness scores compared to the other treatment groups (FIG. 5). Histologically, mice subjected to experimental CDI have pronounced colonic injury with epithelial tissue damage, mucosal edema, and neutrophil infiltration. These findings are not present in mice treated with Lr+DM-maltose (FIG. 6). Mice treated with Lr+DM-maltose have significantly decreased histologic injury scores (FIG. 1) and increased survival (FIG. 2) compared to all other groups.

Dosing

In this example, single dose of Lr in a viable biofilm state [Lr (2×10$^8$ CFU)+DM (2 mg)] is sufficient to reduce the incidence and severity of experimental CDI. The established experimental murine model of CDI with its associated clinical and histologic injury scoring systems to assess for disease severity. Initial studies demonstrate that Lr+DM-maltose is an effective formulation to prevent experiment CDI. DM (20 mg) is incubated overnight in a 1M maltose solution (40 μl). Separately, a high CFU culture of a single strain of Lr is grown and split into 1 ml aliquots. The bacterial suspension is pelleted and resuspended in the DM+maltose solution for 30 minutes prior to use. To induce CDI, C57BL/6 mice receive UV-sterilized water with an antibiotic cocktail to drink ad libitum for 4 days. The cocktail contains kanamycin (0.4 mg/mL), gentamicin (0.035 mg/mL), colistin (850 U/mL), metronidazole (0.215 mg/mL), and vancomycin (0.045 mg/mL). Two days later, mice receive an IP injection of clindamycin (10 mg/kg). Two days after that, mice receive a standardized dose of *C. difficile* (1.5×10$^7$ CFU) via gastric gavage. Different doses of Lr (2×10$^7$, 2×10$^8$, and 2×10$^9$ CFU) and of DM (0.5, 1.0, 5.0 and 10.0 mg/ml) are used. DM hydrated with sterile water only serves as a control for luminal cargo. All Lr+DM doses are administered via gastric gavage 1 day prior to *C. difficile* exposure.

Clinical sickness score. Mice are monitored daily to assess for symptoms and assigned a clinical sickness score daily. Scores≥6 are considered consistent with *C. difficile* colitis. If mice appear moribund prior to completion of the experiment (Day 6 post-inoculation), they are sacrificed, and their clinical sickness scores noted. All survivors to Day 6 are sacrificed. Days of survival post-inoculation of *C. difficile* are noted.

Histological injury score. Colon samples are collected, fixed in 10% formalin, paraffin-embedded, and cut into 5 μm sections, and stained with hematoxylin and eosin. Scoring will be done independently by two blinded reviewers (myself and a board-certified pathologist that helped us develop this scoring system) using our standardized histologic injury scoring. Scores 4 will be defined as consistent with *C. difficile* colitis.

Banana broth assay for determination of *C. difficile* in stool. Stool samples are collected on the day of, or one day prior to *C. difficile* inoculation and at sacrifice. To assess for the presence of *C. difficile*, stool are swabbed with a sterile flocked swab saturated with sterile saline, placed in *Clostridium difficile* Banana Broth™ (Hardy Diagnostics, Santa Maria, CA) and incubated at 37° C. for 24 h. Color change indicates presence (yellow) or absence (red) of *C. difficile*.

qPCR of luciferase-Lr for quantification of Lr in stool. Stool samples from each mouse are collected for qPCR to determine the presence and abundance of Lr for each treatment group. Standards are performed using the initial stock bacterial strains used for incubation on DM. qPCR primers (F-5' CCACTTGCTAAGGAGGTTGC 3' (SEQ ID NO: 1), R-5'GGCAGCCATTAAGGGTGTAA 3' (SEQ ID NO: 2)) against a plasmid-based, click beetle luciferase gene have already been developed and are specific to the luciferase gene. qPCR are performed with an Applied Biosystems Quant Studio 3 PCR machine with Power SYBR Green master in a 30 μl reaction with 250 nM of each primer and 2.5 μl of extracted DNA. qPCR conditions will be: 95° C. for 10 minutes, 40 cycles of 95° C. for 15 seconds, and 59° C.

for 1 minute. Amplicon specificity will be verified by melt curve analysis. Abundance will be quantified in amplicons per gram of contents.

Frequency of Administration. Once the optimal doses of Lr and DM are determined, they are used to determine the optimal frequency of administration. Mice receive daily doses of Lr+DM-maltose starting 1, 2, 3 or 4 days prior to *C. difficile* exposure. When a critical window of intervention is determined, doses are administered once, twice, or three times daily until the time of *C. difficile* exposure. Control groups include mice subjected to experimental CDI with saline only. Experimental endpoints to be determined are as described above.

Prevention

Treatment of Established CDI. Lr is incubated with DM-maltose as above. Induction of CDI in mice is performed as above. Mice receive a cocktail of antibiotics orally followed by an IP dose of clindamycin, followed by a dose of *C. difficile* ($1.5 \times 10^7$ CFU) by gastric gavage as described above. Mice receive a single dose of a Lr+DM-maltose on Day 1, 2, 3, or 4 after *C. difficile* inoculation. Animals are assigned a daily clinical sickness score. Surviving animals will be sacrificed on Day 6 post-inoculation, the colon harvested, and histologic sections prepared for blinded histologic injury scoring as described herein.

Clinical Endpoint Study

Lr is unique in its ability to produce biofilm, the antibacterial reuterin, and the anti-inflammatory compound histidine. Lr significantly increases efficacy when it is administered as a biofilm. This experiment identifies and measures molecular markers of infection and inflammation to evaluate whether the antimicrobial or anti-inflammatory properties, or both, of Lr add to its efficacy.

Genetic knockout viability. Genetic knockouts of Lr that are deficient in reuterin production (ΔgldC) or histamine production (ΔhdcA) are known in the art. Lack of reuterin and histamine production have been confirmed by colorimetric assay for reuterin production and ELISA for histamine production, respectively. These mutant bacterial strains are incubated with DM as above, and tested for prophylactic efficacy in the experimental model of CDI as described above. Controls for these experiments are planktonic Lr and wild-type Lr incubated on DM. Days of survival and clinical sickness scores are recorded for each animal. At the conclusion of the trial, colon samples from all mice are collected for histology and scored using the histologic injury scoring system.

Inflammation markers. Gene expression of TcdA and TcdB from stool samples from mice are analyzed via qPCR to evaluate for pathogenicity of *C. difficile*. Molecular markers of inflammation are measured as follows. RNA will be isolated from colon specimens and subjected to RT-PCR for inflammatory cytokines (TNF-α, IL-1β, IL-6, IL-12, IFN-γ, IL-23, IL-17), chemokines (e.g., CXCL1, CCL2), and antimicrobial peptides (α- and β-defensins).

Microbiome analysis. Fecal samples are collected prior to *C. difficile* inoculation and at the time of sacrifice, and bacterial DNA extracted. After creating DNA libraries, 250× 250 paired end reads of the V4-V5 hypervariable region of the bacterial 16S rRNA gene (using the 515F and 806R primers) are sequenced using a MiSeq2000 (Illumina Inc., San Diego, CA). Microbiome α- and β-diversity are determined to characterize overall community structure of the microbiome. β-diversity is assessed and visualized using principal coordinate analysis (PCoA) plots. Measures of microbiome α-diversity, namely Chao1 (species richness) and Shannon's Diversity Index (SDI; species richness and evenness), are determined using the QIIME2 pipeline (http: qiime2.org) and analyzed by mixed factor ANOVA with treatment as a between subjects factor and sampling time point as a repeated factor. The relative abundances of bacterial genera (and when possible putative species) are analyzed by the machine learning algorithm Random Forest (RF), alongside Boruta feature selection, to derive a list of bacteria that best characterize samples between treatment groups.

Chi-square tests are used for incidence and severity of CDI between all groups of animals. Unless mentioned specifically above, all other endpoints will be compared using one-way and two-way ANOVA with Tukey-Kramer or Newman-Keuls post hoc analysis. Statistical significance for all tests will be set at $p < 0.05$.

TABLE 3

| Physical properties of Sephadex ® dextranomer microspheres | | | | | | | | |
|---|---|---|---|---|---|---|---|---|
| | Dry bead size (µm) | | Wet bead size (µm) | | Permeability | Fractionation [Mr] globular | Fractionation [Mr] | Exclusion limit | Swelling factor |
| Gel type | Low | High | Low | High | K* | proteins | dextrans | (Da) | (ml/g) |
| G-10 | 40 | 120 | 55 | 165 | 19 | 700 | 700 | >700 | 2-3 |
| G-15 | 40 | 120 | 60 | 180 | 18 | 1,500 | 1,500 | >1,500 | 2.5-3.5 |
| G-25 superfine | 10 | 40 | 17 | 70 | 9 | 1,000-5,000 | 100-100 | >5,000 | 4-6 |
| G-25 fine | 20 | 80 | 35 | 140 | 30 | 1,000-5,000 | 100-100 | >5,000 | 4-6 |
| G-25 medium | 50 | 150 | 85 | 260 | 80 | 1,000-5,000 | 100-100 | >5,000 | 4-6 |
| G-25 coarse | >100 | # | 87 | 510 | 290 | 1,000-5,000 | 100-5,000 | >5,000 | 4-6 |
| G-50 superfine | 20 | 50 | 20 | 80 | 13.5 | 1,000-30,000 | 500-10,000 | >30,000 | 9-11 |
| G-50 fine | 20 | 80 | 34 | 208 | 36 | 1,000-30,000 | 500-10,000 | >30,000 | 9-11 |
| G-50 coarse | 100 | 300 | 200 | 610 | 400 | 1,000-30,000 | 500-10,000 | >30,000 | 9-11 |
| G-75 superfine | 20 | 50 | 22 | 143 | # | 3,000-70,000 | 1,000-100,000 | >70,000 | 12-15 |
| G-75 | 40 | 120 | 90 | 280 | # | 3,000-80,000 | 1,000-50,000 | >70,000 | 12-15 |
| G-100 superfine | 10 | 40 | 25 | 100 | # | 4,000-100,000 | 1,000-100,000 | >100,000 | 15-20 |
| G-100 | 40 | 120 | 100 | 310 | # | 4,000-150,000 | 1,000-100,000 | >150,000 | 15-20 |

*Darcy's Law: $U = K\,(\Delta P)\,(L^{-1})$
U = linear flow rate in cm/h;
ΔP = pressure drop over bed in cm H20;
L = bed height in cm;
K = specific permeability constant of particle size and water regain;
not provided by manufacture Experiment No. 2

Materials and Methods

Patent and technical literature are referenced herein by an Arabic number, the citations for which are found immediately preceding the claims. All experiments and procedures were reviewed and approved by the Nationwide Children's Hospital Institutional Animal Care and Use Committee (IACUC Protocol #AR16-00095).

Animals

A combination of mice (conventional C57BL/6 mice) bred in house and commercially obtained (Jackson Laboratories, Bar Harbor, ME) were utilized. Only fully weaned 8- to 10-week old mice were utilized. All mice were housed under identical conditions in groups of no less than 3 and no greater than 5 mice per cage. They were fed an irradiated, soy-free, low-fat rodent diet product #2920x.10 (Harlan, Indianapolis, IN). UV-sterilized drinking water was provided ad lib. Animals were housed in a room designated only for C. difficile experimentation. All bedding and enrichment toys were autoclaved to avoid introduction of outside microbes.

Antibiotic Administration

Antibiotics were administered over the course of 4 days in the form of a water cocktail as previously described[10]. The water cocktail contained kanamycin (0.4 mg/mL), gentamicin (0.035 mg/mL), colistin (850 U/mL), metronidazole (0.215 mg/mL), and vancomycin (0.045 mg/mL), in the manner described by Julia et al[14] and by Chen et al.[15] Antibiotics were purchased from Sigma-Aldrich (St. Louis, MO), reconstituted in sterile water, and provided to the mice ad libitum in their drinking water. The antibiotic concentrations were calculated based on an average weight of the mice used (20-25 gm), and expected water consumption over four days (4-6 mL/mouse/day). 24 hours after antibiotic cocktail completion, an intraperitoneal (IP) injection of clindamycin (10 mg/kg) prepared in sterile water was administered.

Clostridium Difficile

Clostridium difficile was prepared as described in the literature.[10] Vegetative (non-sporulated) C. difficile was prepared from a stock strain of VPI 10463 (ATCC 43255), which was purchased from the American Type Culture Collection (Manassas, VA). C. difficile was grown anaerobically in Modified Reinforced Clostridial Medium (ATCC medium 2107). To remove dissolved oxygen to facilitate C. difficile growth, the medium was degassed by briefly boiling while bubbling with $N_2$ gas and reduced with 4 mM L-Cysteine, followed by pH adjustment to 6.8. C. difficile was grown in an anaerobic chamber in an atmosphere of 5% $H_2$/10% $CO_2$/85% $N_2$ at 37° C. for 48 hours. Bacteria were centrifuged for 5 minutes at 8000×g, the media removed, and the pellet washed twice and resuspended with sterile degassed PBS in an anaerobic atmosphere. The final dosage per animal achieved was $1.5×10^7$ CFU of vegetative C. difficile in 150 Individual aliquots were made under anaerobic conditions to minimize oxygen exposure during mouse treatment.

The optimum dosage of vegetative C. difficile needed to establish colitis was determined in preliminary experiments. This was accomplished by gastric gavage of varying colony forming units (CFUs) ($10^6$, $10^7$, $10^8$ and $10^9$) after receipt of the oral antibiotic cocktail and IP clindamycin. In addition to varying CFUs, different incubation time periods were also tested, obtaining vegetative cultures at 24 hours, 36 hours, and 48 hours of growth. The dosage of $1.5×10^7$ CFU grown in culture medium for 48 hours prior to administration was chosen based on the findings that this dose led to C. difficile colitis in a substantial number of mice but was not uniformly lethal. Each mouse received 150 µL of C. difficile solution by gastric gavage.

Lr Biofilm Preparation

Human-feces derived L. reuteri 23272 (American Type Culture Collection; ATCC, Manassas, VA) was grown overnight in de Man, Rogosa, and Sharpe (MRS) broth (Fisher Scientific, Pittsburgh, PA) at 37° C. in 5% $CO_2$. For planktonic L. reuteri, $1×10^9$ CFU/mL was pelleted and resuspended in sterile 0.9% saline prior to gastric gavage.

For L. reuteri administered with unloaded microspheres, sterile dry dextranomer microspheres (Sephadex G-25 Superfine, GE Healthcare Bio-Sciences, Pittsburgh, PA) were hydrated in a sterile saline solution overnight. For L. reuteri administered with maltose-loaded microspheres, the microspheres were hydrated in a 1M maltose solution in normal saline overnight. All microspheres were removed from the overnight solution via vacuum filter and aseptically transferred into a tube containing the resuspended bacteria. The bacteria were allowed to incubate with the microspheres for 1 hour at room temperature to facilitate binding. Each mouse received 200 µL of the bacterial solution by gastric gavage, for a final dose of $1×10^8$ CFU of Lr.

Experimental Model

The experimental scheme of the C. difficile colitis models for prophylactic and therapeutic treatments are illustrated in FIG. 7 and FIG. 8 respectively. The experimental models span a 15-day time period. In the prophylaxis experiments, following randomization into control or treatment groups, mice to be subjected to the C. difficile protocol were provided an antibiotic cocktail in sterilized drinking water over 4 days (days –8 to –4). Two days after oral antibiotic administration, mice received a single IP injection of clindamycin (day –2). 24 hours after IP clindamycin, mice randomized to treatment groups received one dose of: (1) saline (2) planktonic (Lr), or (3) Lr+DM-maltose. A single gastric gavage dose of C. difficile was administered 24 hours after prophylactic treatment. Control mice received no antibiotics in their drinking water, saline gavage instead of probiotics gavage, and saline injection instead of C. difficile injection. Mice were observed for 6 days post treatment.

In the therapeutic experiments, following randomization into vehicle control and treatment groups, mice to be subjected to the C. difficile protocol again received an antibiotic cocktail over 4 days (days –8 to –4) followed 2 days later by a single IP injection of clindamycin (day –2). 24 hours after the IP clindamycin, mice received a single dose of C. difficile. 24 h later, mice randomized to treatment groups received one dose of: (1) saline (2) planktonic Lr, (3) Lr+DM-water, or (4) Lr+DM-maltose. Control mice received no antibiotics in their drinking water, saline injection instead of C. difficile injection, and saline gavage instead of probiotics gavage. Mice were observed for 6 days post C. difficile inoculation.

Mice were weighed every other day. Symptoms of disease (stool characteristics, weight loss, and decreased response to stimuli) were recorded and mortality was tracked. Animals judged to be in a moribund state were euthanized. Tissue samples from the cecum and colon were taken for histopathologic analysis.

Clinical Sickness Scoring and Histopathologic Analysis

Mice were assigned clinical sickness scores (CSS) and histologic injury scores (HIS) as previously described[10]. Briefly, CSS is based on clinical symptoms of stool characteristics, behavioral change, and percent weight loss (FIG. 9). Each category is scored from 0 to 4, and the individual values are added to provide an overall score (FIG. 9). A CSS of 6 or greater is considered consistent with *C. difficile* colitis (FIG. 9). Animals achieving a CSS of ≥6 were euthanized. Upon sacrifice, the entire colon and cecum were collected for analysis. Histologic injury was graded based on epithelial tissue damage, amount of edema, and neutrophil infiltration (FIG. 10). Each category was scored from 0-3 with the individual values added for an overall score. An HIS of ≥4 is indicative of *C. difficile* colitis (FIG. 10).

Statistical Methods

Survival was assessed by Kaplan-Meier survival analysis and tested using the log-rank test. CSS and HIS were assessed using two-sample t-tests and chi-square/Fisher exact tests. All analyses were conducted using the SAS 9.4 statistical software program (SAS Institute, Cary, NC) with two-sided p-values<0.05 considered statistically significant.

Results

*Lactobacillus reuteri* administered prophylactically in its biofilm state decreases the incidence and severity of *C. difficile* colitis For these experiments, probiotics were administered as prophylaxis prior to *C. difficile* administration.

CSS: Control mice that were not subjected to the *C. difficile* protocol did not develop signs of sickness. Compared to control mice, 67% of mice subjected to the *C. difficile* protocol that received saline only had CSS scores consistent with *C. difficile* infection (p=<0.05) (FIG. 11). 51% of those animals had severe clinical signs of sickness with CSS≥9. There was no significant difference in the incidence of clinical sickness in mice subjected to the *C. difficile* protocol that had prophylaxis with planktonic Lr compared to mice that received saline only (55% vs. 67%; p=0.2594). However, compared to mice that received saline only, mice that received prophylaxis with a single dose of Lr+DM-maltose (Lr in its biofilm state) had a significantly lower incidence of clinical signs consistent with *C. difficile* infection (19% vs 67%; p<0.05).

HIS: Control mice that were not subjected to the *C. difficile* protocol did not develop histologic injury. Compared to control mice, 77% of mice subjected to the experimental *C. difficile* protocol that received saline only had HIS scores consistent with *C. difficile* infection (p<0.05) (FIG. 12). 47% of those animals had severe histological injury with HIS≥7. There was no significant difference in the incidence of histologic injury in mice subjected to the *C. difficile* protocol that had prophylaxis with planktonic Lr compared to mice that received saline only (62% vs 77%, p=0.4872). However, compared to mice that received saline only alone, mice that received prophylaxis with a single dose of Lr+DM-maltose (Lr in its biofilm state) had a significantly lower incidence of histologic injury consistent with *C. difficile* infection (19% vs. 77%; p<0.05).

*Lactobacillus reuteri* administered therapeutically in its biofilm state decreases the incidence and severity of *C. difficile* colitis For these experiments, probiotics where was administered as treatment after *C. difficile* infection was already established.

CSS: Control mice that were not subjected to the *C. difficile* protocol did not develop signs of sickness. Compared to control mice, 67% of mice subjected to the experimental *C. difficile* protocol that received saline only had CSS scores consistent with *C. difficile* infection (p<0.05) (FIG. 13). All of these animals had severe signs of sickness (CSS≥9). There was no significant difference in the incidence of clinical sickness in mice subjected to the *C. difficile* protocol that were treated with planktonic Lr compared to mice that received saline only (56% vs. 67%; p=0.4532).

However, compared to mice that received saline only, mice that received a single dose of Lr+DM-water had a decreased incidence of clinical signs consistent with *C. difficile* infection (36% vs. 67%; p=0.1008), and mice treated with Lr+DM-maltose had a further decrease in the incidence of CSS (29% vs 67%; p<0.05).

HIS: Control mice that were not subjected to the *C. difficile* protocol did not develop histologic injury. Compared to control mice, 66% of mice subjected to the *C. difficile* protocol that received saline only had HIS scores consistent with *C. difficile* infection (p<0.05) (FIG. 8). 53% of those animals had severe histological injury with HIS≥7. There was no significant difference in the incidence of histologic injury in mice subjected to the *C. difficile* protocol that were treated with planktonic Lr compared to mice that received saline only (49% vs. 66%, p=0.501).

However, compared to mice that received saline only, mice that received a single dose of Lr+DM-water had a decreased incidence of histologic injury consistent with *C. difficile* infection (36% vs. 66%; p=0.112), and mice treated with Lr+DM-maltose had a further and significant decrease in the incidence of histologic injury (21% vs 66%; p<0.05).

Discussion

The incidence of *C. difficile* colitis is rising in both pediatric and adult populations.[1,16] Despite this, management of *C. difficile* colitis still requires optimization. At present, the instigator that leads to development of *C. difficile*, antibiotics, is the first-line treatment option for both initial and recurrent *C. difficile* colitis.[6,9,16] However, in spite of these established therapies, many patients often have a number of recurrent infections that are resistant to antibiotic therapy. Additionally, disease in some patients can escalate in severity rapidly, leaving no other treatment option but surgical intervention.[9,17,18]

With the continued rise in the incidence of initial and recurrent disease, as well as associated complications, there has been an increased interest in the development of alternative therapies. In particular, probiotics have been of significant interest in the treatment and prevention of *C. difficile* colitits.[3,9] Probiotics are theoretically efficacious because of their potential to restore an intact gastrointestinal microbiota after disruption by antimicrobials.[19] However, to date, only moderate efficacy of the several probiotics used has been obtained.[20-23] It is important to note that in all of these studies and analyses, probiotics were evaluated in the prevention of *C. difficile* colitis and not in the treatment of the disease. Furthermore, in all of these studies, probiotics were administered in their planktonic state and required repeated doses to demonstrate efficacy.[24,25] In the current study, Applicants have demonstrated that administration of one single dose of Lr in its biofilm state can significantly reduce the incidence and severity of *C. difficile* colitis when administered either prophylactically or therapeutically.

Lr is present in the healthy human intestinal tract and was originally isolated from human breast milk.[26,27] The current studies utilized clade II Lr (ATCC 23272) originally isolated from human stool. This strain of Lr, among others, has antimicrobial activity conferred by its ability to convert glycerol into the antimicrobial compound reuterin, and it has anti-inflammatory properties due to its ability to produce histamine and to modulate cytokine production.[28,29] Lr also readily forms a biofilm and has a significant affinity for the cross-linked dextran in DM.

Because of these properties, as well as the inventors' experience with the probiotic in the prevent of necrotizing enterocolitis (NEC),[12,13] Lr was chosen for the experimental model.

In the current study, no efficacy of a single dose of Lr administered in its planktonic state either prophylactically or therapeutically was found. Other strains of planktonic Lr have demonstrated various levels of efficacy with repeated multi-dose delivery in other studies.[3,20,30] On the other hand, efficacy was demonstrated with the administration of just one single dose of Lr administered in its biofilm state. It had been shown that Lr in its biofilm state demonstrates prolonged survival in acidic environments and improved adherence to intestinal epithelial cells in vitro[11,13] and protects the intestines from NEC in vivo.[12,13] In these studies, augmentation of biofilm formation by adherence of Lr to DM loaded with sucrose or maltose leads to increased intestinal protection,[12] and conversely, decreasing the ability of Lr to produce a biofilm by using a genetically altered strain of Lr ($\Delta$gtfW) decreases intestinal protection.[12] Similar results were found for both in clinical sickness and histological injury (FIG. 13 and FIG. 14). The best efficacy was noted in for the formulation of Lr adhered to maltose-loaded DM, where there is greatest biofilm formation.

The adherence of Lr to DM to promote biofilm formation is a central component of its improved protective effect seen in this study. Lr adheres to DM via the expression of glucan-binding proteins, regulated by the GtfW enzyme.[12] It is important to note that only a few bacteria make glucan homopolymers that facilitate binding to DM. Importantly, it was shown that Escherichia coli, Salmonella typhimurium, and Clostridium difficile do not detectably bind to DM,[11] allaying any concerns that administration of DM might provide a platform for increased biofilm formation in pathogenic bacteria.

Experiment No. 3

Assessment of lyophilized DMs: To preliminarily assess whether lyophilized DM are as effective non-lyophilized DM, Applicant prepared an intermediary version called "L-DM". Assessment of the L-DM is comparable to DM was done using in vitro assessments of microsphere adherence, intestinal epithelial cell (IEC) adherence, and acid survival. For L. reuteri adherence to microspheres, L. reuteri was incubated with DM for 5 min and non-adhered L. reuteri were separated by low-speed centrifugation in a spin column containing a filter that prevents microspheres and adhered L. reuteri from passing through. Non-adhered L. reuteri were quantified using plate counts and subtracted from the starting CFU to quantify DM-adhered L. reuteri. For adherence to IEC, L-DM was incubated on a confluent layer of HT-29 IEC for 1 h, after which non-adhered L. reuteri were removed by repeated washing. IEC and adhered L. reuteri were then enzymatically dislodged from the plate, and adhered-L. reuteri CFU were determined via plate counts. For acid survival studies, DM and L-DM were diluted 1:100 in synthetic gastric acid and assessed for viability using plate counts after 4 h of exposure to pH 2. Collectively, these data demonstrate that L-DM performs as well as DM (data not shown).

Establishment of CDI scoring systems and confirmation of CDI in stool. To evaluate the efficacy of L-DM in a CDI animal model, Applicant developed a standardized scoring system that uses a clinical sickness score (CSS) and a defined histologic injury score (HIS). The experimental scheme of the model is shown in FIG. 4. C57/BL6 mice were randomly assigned to the following groups: 1) vehicle control (received antibiotic-free drinking water, an equivalent volume of saline IP instead of clindamycin, and an equivalent volume of saline by gavage instead of C. difficile); 2) antibiotics only (received antibiotic cocktail and no C. difficile); or 3) antibiotics plus C. difficile (received the antibiotic cocktail, clindamycin, and C. difficile). The antibiotic cocktail was administered in water ad libitum from day −8 to −4 prior to C. difficile infection and contained kanamycin (0.4 mg/mL), gentamicin (0.035 mg/mL), colistin (850 U/mL), metronidazole (0.215 mg/mL), and vancomycin (0.045 mg/mL). (Riegler (2001) Techniques in Coloproctology, Springer, 2001; Degnan, Cell Metab (2008) 74:3291-3294, 2008): Clindamycin was delivered 48 hours prior to infection as an intraperitoneal (IP) injection (10 mg/kg prepared in water). C. difficile VPI 10463 (ATCC 43255) was prepared under anaerobic conditions and a final dosage per animal of $1.5 \times 107$ CFU of vegetative C. difficile was given via oral gavage.

Banana Broth Assay to detect C. difficile. Stool samples were collected the day prior to C. difficile administration and on the day of sacrifice for detection of C. difficile using the standard Banana Broth™ culture assay (Hardy Diagnostics). This assay utilizes a selective and differential Brucella Broth based growth medium that contains hemin and vitamin K supplements which induce fastidious bacterial growth, as well as components to support the growth of oxygen-reducing microorganisms. Mannitol availability and pH are optimized to promote selective C. difficile growth. The assay has 100% specificity for C. difficile. Stool samples were aseptically swabbed and assessed using manufacturer's instructions. C. difficile was only detected in in mice receiving C. difficile (data not shown). (Shelby (2019) Colitis. J Invest Surg. 1-9).

Effectiveness of L-DM in preventing CDI. The CDI mouse model was used to evaluate the ability of lab-grade L-DM to prevent CDI. The model was executed as described above, with treatments of either saline, L. reuteri alone, or lab-grade L-DM administered on day −1 (one day prior to C. difficile) via oral gavage. Lab grade L-DM was prepared as described above. The effectiveness of L-DM was determined using CSS from daily monitoring of animals and histological analysis of intestines. Treatment with lab-grade L-DM resulted in both a significant reduction in CSS and HIS compared to the saline control with only 19% of the mice in the L-DM group experiencing moderate to severe sickness (FIG. 5A) and histologic injury (FIG. 5B). The histological changes seen with L-DM treatment are striking, with untreated infected animals having substantial epithelial damage, mucosal edema, hemorrhage, and neutrophil infiltration, and L-DM-treated animals showing greatly reduced signs of damage (FIG. 8C). Treatment with L. reuteri alone did not result in significant improvement in CSS, or HIS compared to the saline control, indicating that L. reuteri in its biofilm state as provided by L-DM s necessary for CDI prevention.

Fluorescence in situ hybridization (FISH) and immunofluorescence (IF) to assess mucous thickness and enteric bacterial spatial location in antibiotic-treated mice. Fluorescence in situ hybridization (FISH) alongside immunofluorescence was used to understand how L-DM affects mucosal thickness and commensal bacterial infiltration into the mucous layer or onto host colonic tissue. For FISH, universal bacteria were targeted with the EUB338 universal 16S rRNA probe. Anti-sense complementary FISH probes were utilized as internal controls. For immunofluorescence (IF), the host mucous layer was analyzed by targeting fucose (an abundant terminal sugar on mucins) with a fluorophore-conjugated (Alexa 488) lectin (Ulex-Europeaus Agllutinin [UEA-1]). Nuclei of intestinal tissue was stained with Prolong gold antifade with DAPI. Images were generated from a Zeizz LSM 710 Confocal microscope (20× and 63×) and analyzed using a MatLab based software tool (BacSpace) as previously described. (Kralj (2005) Appl Environ Microbiol 71:3942-3950). Contour drawing and machine learning tools available on BacSpace were used to quantify the average distance of the endogenous microbiota (Cy3) in relation to the host epithelia (DAPI) and mucus layers (Alexa 488) within the proximal and distal colon. Animals that received L-DM had greater mucous thickness and distance between the bacteria and epithelium compared to antibiotic+PBS treated animals (as well as untreated control animals) (FIG. 15). This demonstrates that L-DM preserves the protective mucous barrier in antibiotic-treated mice.

CONCLUSION

Lr administered in its biofilm state exhibits a protective effect against *C. difficile* colitis when administered both prophylactically and as a treatment, with just one single dose. These results support the future translation of this treatment to the bedside given the dual efficacy of this probiotic.

Equivalents

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that the materials, methods, and examples provided here are representative of preferred embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

REFERENCES

1. Lessa F C, Winston L G, McDonald L C, Team EIPCdS. Burden of *Clostridium difficile* infection in the United States. *N Engl J Med.* 2015; 372(24):2369-2370.
2. Olsen M A, Young-Xu Y, Stwalley D, et al. The burden of *Clostridium difficile* infection: estimates of the incidence of CDI from U.S. Administrative databases. *BMC Infect Dis.* 2016; 16:177.
3. Mills J P, Rao K, Young V B. Probiotics for prevention of *Clostridium difficile* infection. *Curr Opin Gastroenterol.* 2018; 34(1):3-10.
4. Dieterle M G, Young V B. Reducing Recurrence of *C. difficile* Infection. *Cell.* 2017; 169(3):375.
5. Abt M C, McKenney P T, Pamer E G. *Clostridium difficile* colitis: pathogenesis and host defence. *Nat Rev Microbiol.* 2016; 14(10):609-620.
6. Evans C T, Safdar N. Current Trends in the Epidemiology and Outcomes of *Clostridium difficile* Infection. *Clinical Infectious Diseases.* 2015; 60(suppl_2):S66-S71.
7. Ofosu A. *Clostridium difficile* infection: a review of current and emerging therapies. *Ann Gastroenterol.* 2016; 29(2):147-154.
8. Nicholson M R, Thomsen I P, Slaughter J C, Creech C B, Edwards K M. Novel risk factors for recurrent *Clostridium difficile* infection in children. *J Pediatr Gastroenterol Nutr.* 2015; 60(1):18-22.
9. Maziade P J, Pereira P, Goldstein E J. A Decade of Experience in Primary Prevention of *Clostridium difficile* Infection at a Community Hospital Using the Probiotic Combination *Lactobacillus acidophilus* CL1285, *Lactobacillus casei* LBC80R, and *Lactobacillus rhamnosus* CLR2 (Bio-K+). *Clin Infect Dis.* 2015; 60 Suppl 2:S144-147.
10. Shelby R D, Tengberg N, Conces M, et al. Development of a Standardized Scoring System to Assess a Murine Model of *Clostridium difficile* Colitis. *J Invest Surg.* 2019:1-9.
11. Navarro J B, Mashburn-Warren L, Bakaletz L O, Bailey M T, Goodman S D. Enhanced Probiotic Potential of. *Front Microbiol.* 2017; 8:489.
12. Olson J K, Navarro J B, Allen J M, et al. An enhanced *Lactobacillus reuteri* biofilm formulation that increases protection against experimental necrotizing enterocolitis. *Am J Physiol Gastrointest Liver Physiol.* 2018; 315(3): G408-G419.
13. Olson J K, Rager T M, Navarro J B, Mashburn-Warren L, Goodman S D, Besner G E. Harvesting the benefits of biofilms: A novel probiotic delivery system for the prevention of necrotizing enterocolitis. *J Pediatr Surg.* 2016; 51(6): 936-941.
14. *Julia* V, McSorley S S, Malherbe L, et al. Priming by microbial antigens from the intestinal flora determines the ability of CD4+ T cells to rapidly secrete IL-4 in BALB/c mice infected with *Leishmania major. J Immunol.* 2000; 165(10):5637-5645.
15. Chen X, Katchar K, Goldsmith J D, et al. A mouse model of *Clostridium difficile*-associated disease. *Gastroenterology.* 2008; 135(6):1984-1992.
16. D'Ostroph A R, So T Y. Treatment of pediatric. *Infect Drug Resist.* 2017; 10:365-375.
17. Hall B R, Armijo P R, Leinicke J A, Langenfeld S J, Oleynikov D. Prolonged non-operative management of

*Clostridium difficile* colitis is associated with increased mortality, complications, and cost. *Am J Surg.* 2019; 217(6):1042-1046.

18. Hall J F, Berger D. Outcome of colectomy for *Clostridium difficile* colitis: a plea for early surgical management. *Am J Surg.* 2008; 196(3):384-388.

19. Dinleyici M, Vandenplas Y. *Clostridium difficile* Colitis Prevention and Treatment. *Adv Exp Med Biol.* 2019; 1125:139-146.

20. Guo Q, Goldenberg J Z, Humphrey C, El Dib R, Johnston B C. Probiotics for the prevention of pediatric antibiotic-associated diarrhea. *Cochrane Database Syst Rev.* 2019; 4:CD004827.

21. Goldenberg J Z, Mertz D, Johnston B C. Probiotics to Prevent *Clostridium difficile* Infection in Patients Receiving Antibiotics. *JAMA.* 2018; 320(5):499-500.

28. Spinler J K, Sontakke A, Hollister E B, et al. From prediction to function using evolutionary genomics: human-specific ecotypes of *Lactobacillus reuteri* have diverse probiotic functions. *Genome Biol Evol.* 2014; 6(7): 1772-1789.

29. Spinler J K, Taweechotipatr M, Rognerud C L, Ou C N, Tumwasorn S, Versalovic J. Human-derived probiotic *Lactobacillus reuteri* demonstrate antimicrobial activities targeting diverse enteric bacterial pathogens. *Anaerobe.* 2008; 14(3):166-171.

30. Rao K, Young VB. Probiotics for Prevention of *Clostridium difficile* Infection in Hospitalized Patients: Is the Jury Still Out? *Gastroenterology.* 2017; 152(8):1817-1819.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccacttgcta aggaggttgc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcagccatt aagggtgtaa                                                    20
```

22. Johnson S, Maziade P J, McFarland L V, et al. Is primary prevention of *Clostridium difficile* infection possible with specific probiotics? *Int J Infect Dis.* 2012; 16(11):e786-792.

23. Goldstein E J C, Johnson S J, Maziade P J, et al. Probiotics and prevention of *Clostridium difficile* infection. *Anaerobe.* 2017; 45:114-119.

24. Goldenberg J Z, Yap C, Lytvyn L, et al. Probiotics for the prevention of *Clostridium difficile*-associated diarrhea in adults and children. *Cochrane Database Syst Rev.* 2017; 12:CD006095.

25. Johnston B C, Lytvyn L, Lo C K, et al. Microbial Preparations (Probiotics) for the Prevention of *Clostridium difficile* Infection in Adults and Children: An Individual Patient Data Meta-analysis of 6,851 Participants. *Infect Control Hosp Epidemiol.* 2018; 39(7):771-781.

26. Reuter G. The *Lactobacillus* and *Bifidobacterium* microflora of the human intestine: composition and succession. *Curr Issues Intest Microbiol.* 2001; 2(2):43-53.

27. Urbańska M, Szajewska H. The efficacy of *Lactobacillus reuteri* DSM 17938 in infants and children: a review of the current evidence. *Eur J Pediatr.* 2014; 173(10):1327-1337.

What is claimed is:

1. A method for treating *Clostridium difficile* infection caused by antibiotic induced dysbiosis or reversing antibiotic induced dysbiosis in a subject in need thereof, comprising administering to the subject an effective amount of a composition comprising:

a microsphere comprising cross-linked dextran, a biofilm-generating probiotic bacterium comprising *Lactobacillus reuteri* forming a biofilm coating on the surface of the microsphere, and a water soluble carbohydrate selected from the group consisting of maltose, sucrose, and combinations thereof.

2. A method for restoring the mucosal layer of the intestine in a subject suffering from *Clostridium difficile* infection caused by antibiotic induced dysbiosis, comprising administering to the subject an effective amount of a composition comprising:

a microsphere comprising a cross-linked dextran, a biofilm-generating probiotic bacterium comprising *Lactobacillus reuteri* forming a biofilm coating on the surface of the microsphere, and a water-soluble carbohydrate selected from the group consisting of maltose, sucrose, and combinations thereof, wherein the administration of the effective amount of the composition results in the restoration of the protective mucosal layer of the intestine.

3. The method of claim 1, wherein the administration of the effective amount of the composition results in the restoration of the protective mucosal layer of the intestine.

4. The method of claim 2, wherein the administration of the effective amount of the composition results in the one or more of: maintaining the epithelial barrier, supporting epithelial cell integrity or supporting goblet cell production of mucous.

5. The method of claim 2, wherein the microsphere further comprises a complete biofilm coating on the external surface of the microsphere.

6. The method of claim 2, wherein the diameter of the microsphere is from 1 to 75 microns.

7. The method of claim 2, wherein the microsphere further comprises one or more of: a prebiofilmic, a therapeutic drug or agent, a chemical reductant, a molecule that promotes adsorption to the surface of the microsphere, a molecule that supports absorption of the microsphere.

8. The method of claim 2, wherein the probiotic bacterium further comprises *Lactobacillus acidophilus, L. crispatus, L. gasseri*, group *L. delbrueckii, L. salivarius, L. casei, L. paracasei, L. plantarum, L. rhamnosus, L. reuteri, L. brevis, L. buchneri, L. fermentum, L. rhamnosus, Bifobacterium adolescentis, B. angulation, B. bifidum, B. breve, B. catenulatum, B. infantis, B. lactis, B. longum, B. pseudocatenulatum, Streptococcus thermophiles, Pseudomonas fluorescens, P. protegens, P. brassicacearum, P. aeruginosa; Azospirillum brabrasilense, A. lipferum, A. halopraeferens, A. irakense; Acetobacter diazotrophicus; Herbaspirillum seropedicae; Bacillus subtilis, Pseudomonas stutzeri, fluorescens, P. putida, P. cepacian, P. vesicularis, P. paucimobilis; Bacillus cereus, B. thuringiensis, B. sphaericus; Shewanella oneidensis; Geobacter bemidjiensis, G. metallireducens, G. sulfurreducens, G. uraniireducens, G. lovleyi; Serratia marcescens, Desulfovibrio vulgaris, D. desulfuricans, Dechloromonas aromatic, Deinococcus radiodurans, Meth-*

*ylibium petroleiphilum, Alcanivorax borkumensis, Archaeglobus fulgidus, Haloferax* sp., *Halobacterium* sp., and combinations thereof.

9. The method of claim 2, wherein the microsphere encapsulates the water-soluble carbohydrate within a hollow core.

10. The method of claim 2, wherein the cross-linked dextran is dextran cross-linked with epichlorohydrin.

11. The method of claim 2, wherein the surface of the microsphere is porous and/or semi-permeable and the water-soluble carbohydrate is released by diffusion or the microsphere slowly degrades causing leaks and diffusion from the microsphere.

12. The method of claim 2, wherein the composition is administered to provide from $1\times10^7$ to $1\times10^9$ CFU/ml of the biofilm-generating probiotic bacterium.

13. A method for preventing or treating *Clostridium difficile* colitis in a subject having antibiotic induced dysbiosis, comprising administering a composition comprising:

$1\times10^7$ to $1\times10^{10}$ CFU/ml of *Lactobacillus reuteri*; and a plurality of microspheres each comprising: cross-linked dextran, and a water-soluble carbohydrate selected from the group consisting of maltose, sucrose, and combinations thereof, and wherein *Lactobacillus reuteri* forms a biofilm coating on the surface of the microsphere.

14. The method of claim 2, wherein release of the prebiotic is regulated by varying microsphere size or by altering the viscosity of the prebiotic.

15. The method of claim 1, wherein the cross-linked dextran is dextran cross-linked with epichlorohydrin.

16. The method of claim 1, wherein the microsphere further comprises a complete biofilm coating on the external surface of the microsphere.

17. The method of claim 1, wherein the microsphere encapsulates the water-soluble carbohydrate within a hollow core.

18. The method of claim 17, wherein the surface of the microsphere is porous and/or semi-permeable and the water-soluble carbohydrate is released by diffusion or the microsphere slowly degrades causing leaks and diffusion from the microsphere.

* * * * *